US011076786B2

(12) United States Patent
Choudhury et al.

(10) Patent No.: US 11,076,786 B2
(45) Date of Patent: Aug. 3, 2021

(54) WOUND MONITORING SENSORS AND USE THEREOF

(71) Applicants: Sohini Roy Choudhury, Miami, FL (US); Yogeswaran Umasankar, Homestead, FL (US); Shekhar Bhansali, Weston, FL (US); Robert S. Kirsner, Miami, FL (US); Hadar A. Lev-Tov, Miami, FL (US)

(72) Inventors: Sohini Roy Choudhury, Miami, FL (US); Yogeswaran Umasankar, Homestead, FL (US); Shekhar Bhansali, Weston, FL (US); Robert S. Kirsner, Miami, FL (US); Hadar A. Lev-Tov, Miami, FL (US)

(73) Assignees: THE FLORIDA INTERNATIONAL UNIVERSITY BOARD OF TRUSTEES, Miami, FL (US); UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/589,437

(22) Filed: Oct. 1, 2019

(65) Prior Publication Data
US 2020/0100711 A1     Apr. 2, 2020

Related U.S. Application Data

(60) Provisional application No. 62/739,712, filed on Oct. 1, 2018.

(51) Int. Cl.
*A61B 5/1486* (2006.01)
*A61B 5/20* (2006.01)
(Continued)

(52) U.S. Cl.
CPC ........ *A61B 5/1486* (2013.01); *A61B 5/14507* (2013.01); *A61B 5/14539* (2013.01);
(Continued)

(58) Field of Classification Search
CPC .............. A61B 5/1486; A61B 5/14507; A61B 5/14539; A61B 5/14546; A61B 5/20; A61B 5/4266; A61B 5/4277
(Continued)

(56) References Cited

U.S. PATENT DOCUMENTS

| 5,089,112 A | * | 2/1992 | Skotheim | ............... C12Q 1/004 204/403.1 |
| 5,264,104 A | * | 11/1993 | Gregg | .................... C12Q 1/002 204/403.09 |

(Continued)

OTHER PUBLICATIONS

Bobulescu, I.A., et al., "Renal Transport of Uric Acid: Evolving Concepts and Uncertainties." Adv Chronic Kidney Dis, Nov. 2012, 19(6): 358-371.

(Continued)

*Primary Examiner* — Navin Natnithithadha
(74) *Attorney, Agent, or Firm* — Saliwanchik, Lloyd & Eisenschenk

(57) ABSTRACT

The subject invention provides sensor systems that can detect biomarkers related to wound healing (e.g., uric acid, adenosine, arginine and/or xanthine). In one embodiment, the subject invention pertains to materials and methods for monitoring biomarkers non-invasively in a wound and a biofluid (e.g., sweat) in the proximity of the wound, optionally, including other physiological fluids. Skin based, non-invasive enzymatic electrochemical biosensor on a wearable platform (e.g., sweat patch) that can evaluate the healing of wounds through assessment of its biomarker levels are (Continued)

provided. This non-invasive detection from physiologically biofluids can reduce or eliminate occlusion effects.

17 Claims, 21 Drawing Sheets
(21 of 21 Drawing Sheet(s) Filed in Color)

(51) Int. Cl.
*A61B 5/145* (2006.01)
*A61B 5/00* (2006.01)

(52) U.S. Cl.
CPC ............ *A61B 5/14546* (2013.01); *A61B 5/20* (2013.01); *A61B 5/4266* (2013.01); *A61B 5/4277* (2013.01)

(58) Field of Classification Search
USPC ......................................... 600/309, 345–366
See application file for complete search history.

(56) References Cited

U.S. PATENT DOCUMENTS

| | | | | |
|---|---|---|---|---|
| 5,264,105 | A * | 11/1993 | Gregg | C12Q 1/002 204/403.09 |
| 5,320,725 | A * | 6/1994 | Gregg | C12Q 1/002 204/403.1 |
| 7,045,054 | B1 * | 5/2006 | Buck | A61B 5/14532 204/403.1 |
| 7,731,835 | B2 * | 6/2010 | Buck | A61B 5/14532 204/403.04 |
| 8,597,925 | B2 * | 12/2013 | Hwang | C25D 15/02 435/183 |
| 8,636,884 | B2 * | 1/2014 | Feldman | C12Q 1/004 204/403.12 |
| 8,906,211 | B2 * | 12/2014 | Feldman | C12Q 1/004 204/403.12 |
| 9,309,550 | B2 * | 4/2016 | Cooper | C12Q 1/001 |
| 9,428,785 | B2 * | 8/2016 | Feldman | C12Q 1/004 |
| 9,820,692 | B2 * | 11/2017 | Wang | A61B 5/1477 |
| 9,885,073 | B2 * | 2/2018 | Feldman | C12Q 1/004 |
| 9,986,942 | B2 * | 6/2018 | Brauker | A61B 5/14532 |
| 10,722,160 | B2 * | 7/2020 | Wang | A61B 5/6833 |
| 2001/0016682 | A1 * | 8/2001 | Berner | A61B 5/14532 600/345 |
| 2004/0045879 | A1 * | 3/2004 | Shults | A61B 5/14532 210/85 |
| 2005/0054909 | A1 * | 3/2005 | Petisce | A61B 5/14532 600/345 |
| 2005/0143635 | A1 * | 6/2005 | Kamath | A61B 5/7203 600/347 |
| 2005/0211572 | A1 * | 9/2005 | Buck | A61B 5/14532 205/778 |
| 2006/0142651 | A1 * | 6/2006 | Brister | A61B 5/0031 600/347 |
| 2009/0198117 | A1 * | 8/2009 | Cooper | B82Y 30/00 600/347 |
| 2010/0065441 | A1 * | 3/2010 | Feldman | C12Q 1/004 205/777.5 |
| 2011/0155576 | A1 * | 6/2011 | Hwang | C25D 15/02 204/471 |
| 2014/0141487 | A1 * | 5/2014 | Feldman | C12Q 1/004 435/188 |
| 2015/0090590 | A1 * | 4/2015 | Feldman | C12Q 1/004 204/403.14 |
| 2015/0126834 | A1 * | 5/2015 | Wang | B32B 38/145 600/345 |
| 2017/0051329 | A1 * | 2/2017 | Feldman | C12Q 1/004 |
| 2017/0238851 | A1 * | 8/2017 | Duhamel | A61B 5/14532 |
| 2017/0325724 | A1 * | 11/2017 | Wang | A61B 5/14521 |
| 2019/0004005 | A1 * | 1/2019 | Oja | C12Q 1/004 |
| 2019/0117083 | A1 * | 4/2019 | Wang | A61B 5/053 |

OTHER PUBLICATIONS

Bonnete, F., "Macromolecular Crystallization Controlled by Colloidal Interactions: The Case of Urate Oxidase." Crystallization—science and technology. France: InTech-Open Access Company, Sep. 2012, pp. 349-378.
Borland, L.M., et al., "An Introduction to Electrochemical Methods in Neuroscience." Electrochemical Methods for Neuroscience, CRC press, Dec. 2006, pp. 1-18.
Choudhury, S.R., et al., "A Wearable Electrochemical Sensor to Monitor Progression of Wound Healing." ECS Transactions, Oct. 2017, 80(10): 1345-1353.
Choudhury, S.R., et al., "Uricase Based Enzymatic Biosensor for Non-Invasive Detection of Uric Acid by Entrapment in PVA-SbQ Polymer Matrix." Electroanalysis, Oct. 2018, 30(10): 2374-2385.
Choudhury, S.R., et al., "Nano-composite enzymatic xanthine biosensor for wound diagnostics." In 2018 IEEE Sensors, Oct. 2018, pp. 1-4.
Cobb, M.J., et al., "Noninvasive assessment of cutaneous wound healing using ultrahigh-resolution optical coherence tomography." Journal of Biomedical Optics, Nov. 2006, 11(6): 064002.
Colloc'h, N., et al., "Crystal Structure of the protein drug urate oxidase-inhibitor complex at 2.05 A resolution." Nature Structural Biology, Nov. 1997, 4(11): 947-952.
Daniel, R.M., et al., "The denaturation and degradation of stable enzymes at high temperatures." Biochem. J., 1996, 317: 1-11.
Dargaville, T.R., et al., "Sensors and imaging for wound healing: A review." Biosensors and Bioelectronics, 2012, 41: 30-42.
Fernandez, M.L., et al., "Elevated uric acid correlates with wound severity." International wound journal, Apr. 2012, 9(2): 139-149.
Gethin, G., "The significance of surface pH in chronic wounds." Wounds UK, 2007, 3(3): 52-56.
Huang, C.T., et al., "Uric Acid and Urea in Human Sweat." Chinese Journal of Physiology, 2002, 45(3): 109-115.
Mahler, H.R., et al., "Studies on uricase I. Preparation, purification, and properties of a cuproprotein." Journal of Thological Chemistry, Oct. 1955, 216(2): 625-642.
Maiuolo, J., et al., "Regulation of uric acid metabolism and excretion." International Journal of Cardiology, 2016, 213: 8-14.
Martin, P., "Wound Healing—Aiming for Perfect Skin Regeneration." Science, Apr. 1997, 276(5309): 75-81.
Mohamad, N.R., et al., "Review; Agriculture and Environmental Biotechnology An overview of technologies for immobilization of enzymes and surface analysis techniques for immobilized enzymes." Biotechnology & Biotechnological Equipment, 2015, 29(2): 205-220.
Montain, S.J., et al., "Sweat Mineral-Element Responses During 7 h of Exercise-Heat Stress" International Journal of Sport Nutrition and Exercise Metabolism, 2007, 17: 574-582.
Najee, E.N., et al., "Comparative Study of Biochemical and Bacteriological Analysis of Wound Fluid and Serum from Non Healing and Healing Skin Ulcers." Al-Mustansiriya J. Sci., 2010, 21(4): 53-60.
Nery, R.A., et al., "Uric Acid and Tissue Repair." ABCD. Arquivos Brasileiros de Cirurgia Digestiva (São Paulo), Dec. 2015, 28(4): 290-292.
Peng, Z., et al., "Design of a portable imager for near-infrared visualization of cutaneous wounds." Journal of Biomedical Optics, Jan. 2017, 22(1): 016010, 1-8.
Shoba, E., et al., "Design and development of Papain/Urea loaded PVA nanofibers for wound debridement." RSC Advances, 2014, 4(104): 60209-60215.

* cited by examiner

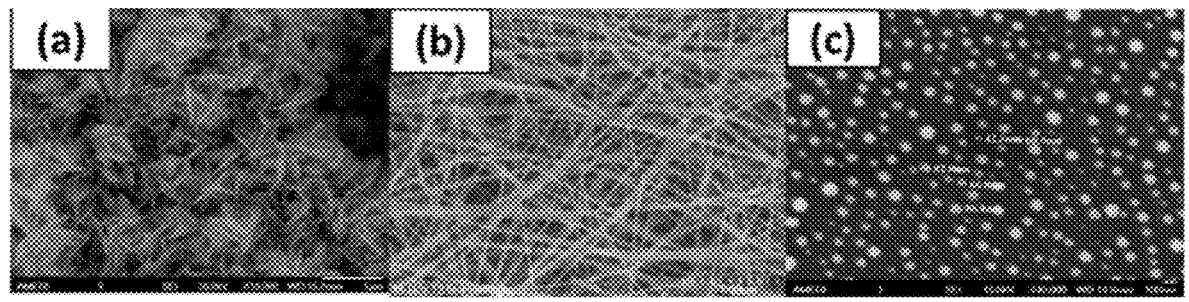
FIG. 6A  FIG. 6B  FIG. 6C
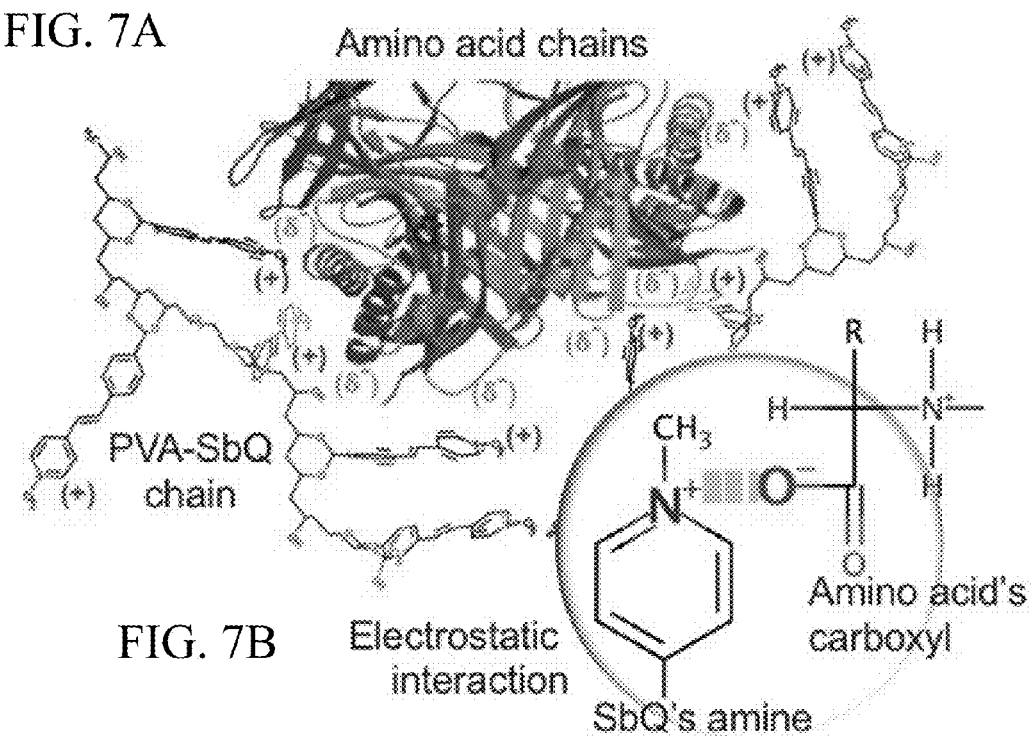
FIG. 7A
FIG. 7B

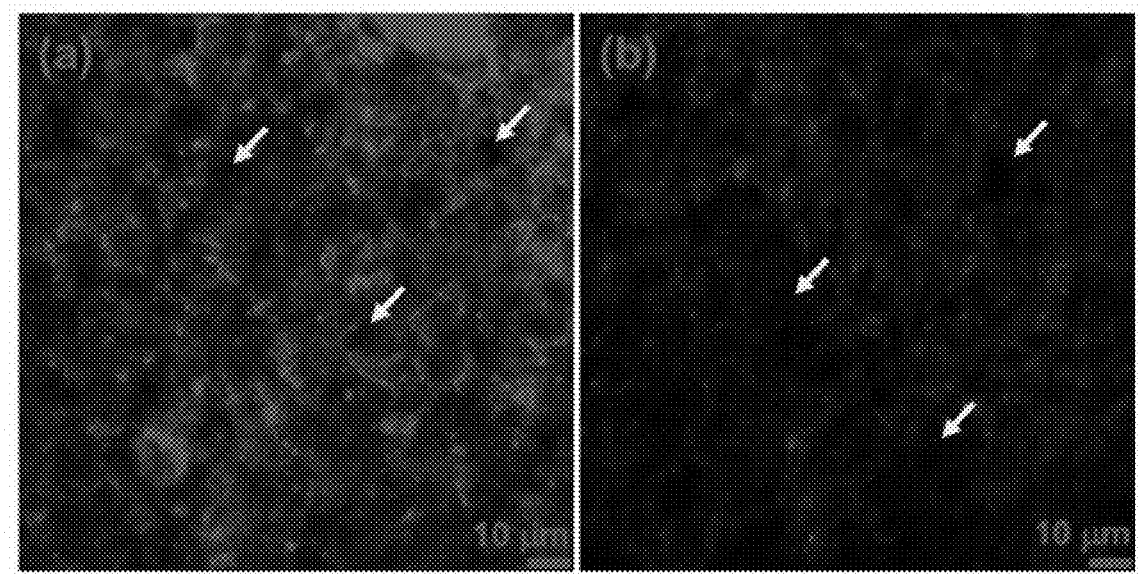
FIG. 10A  FIG. 10B
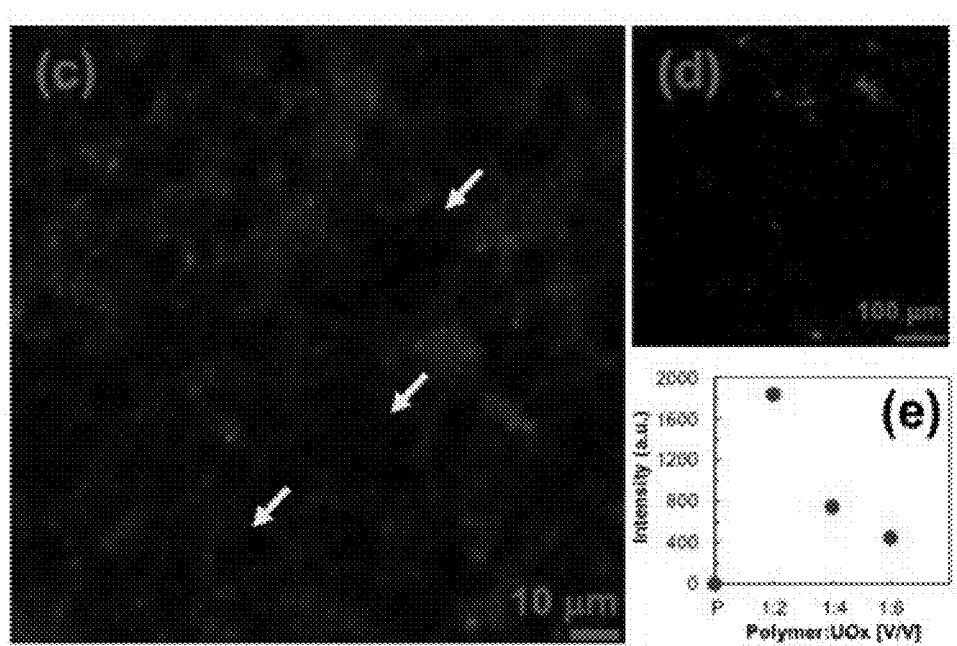
FIG. 10C
FIG. 10D
FIG. 10E

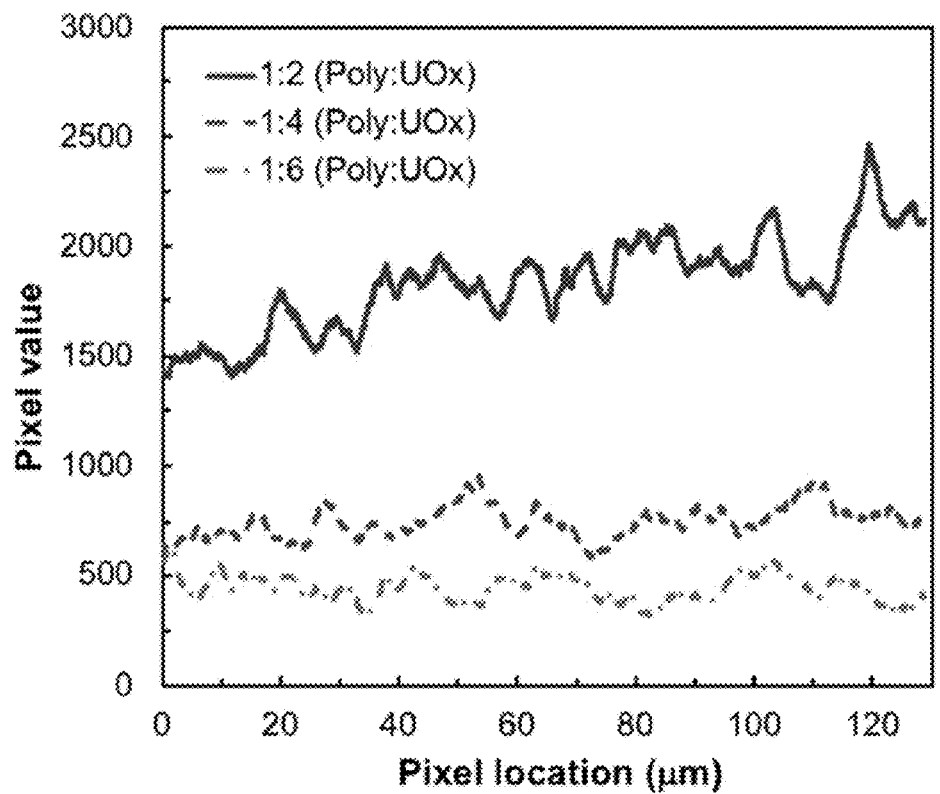
FIG. 11
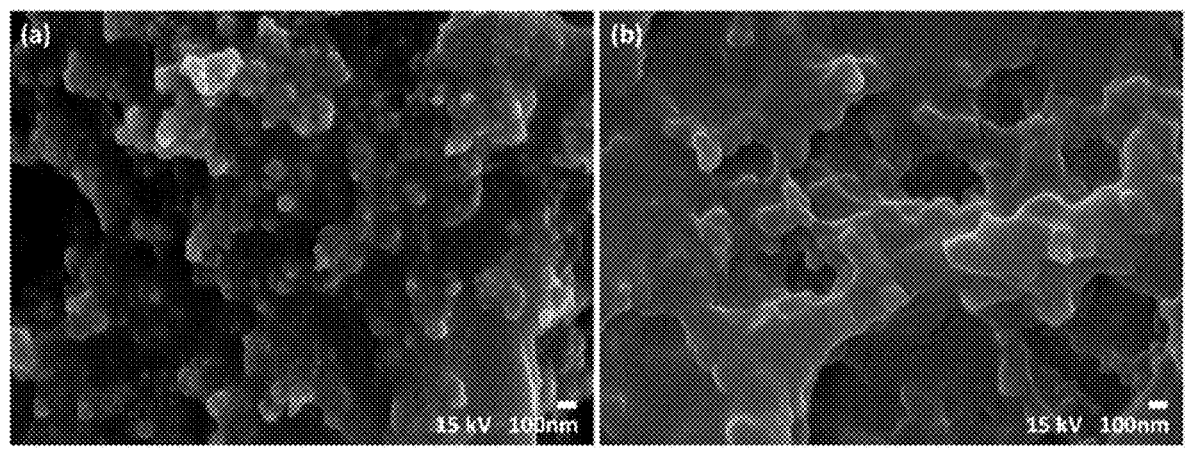
FIG. 12A
FIG. 12B

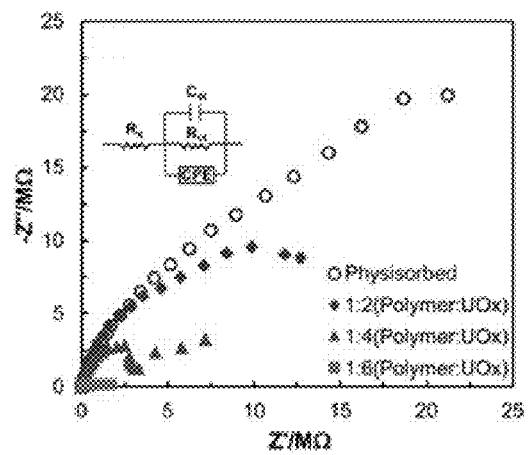
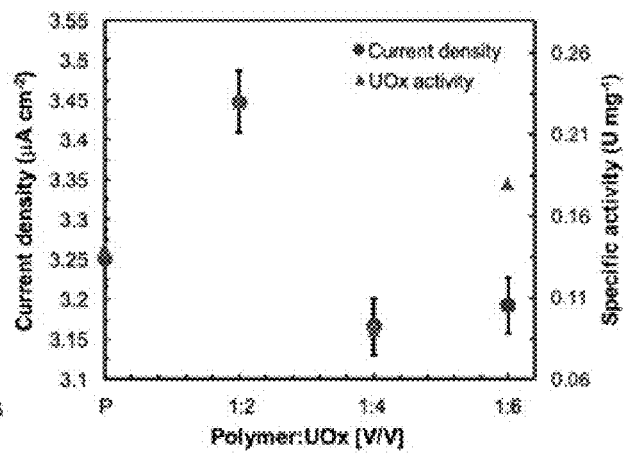
FIG. 13A  FIG. 13B
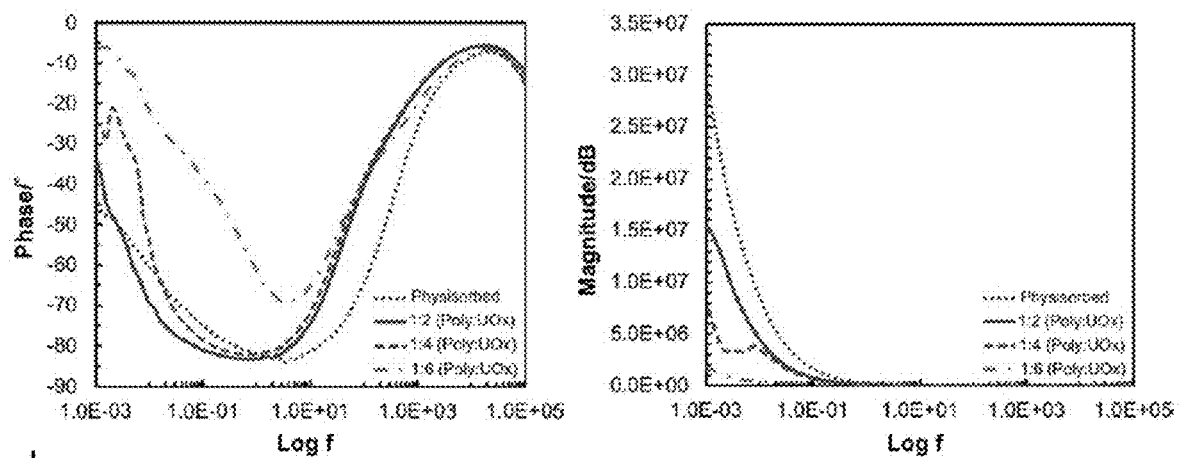
FIG. 14

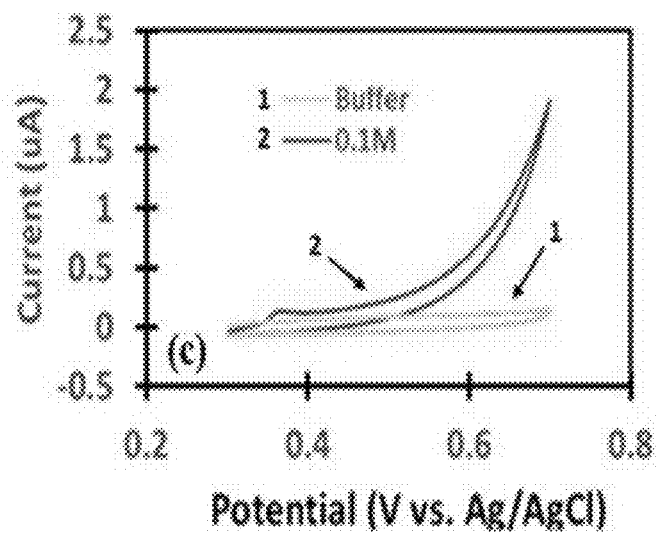
FIG. 15
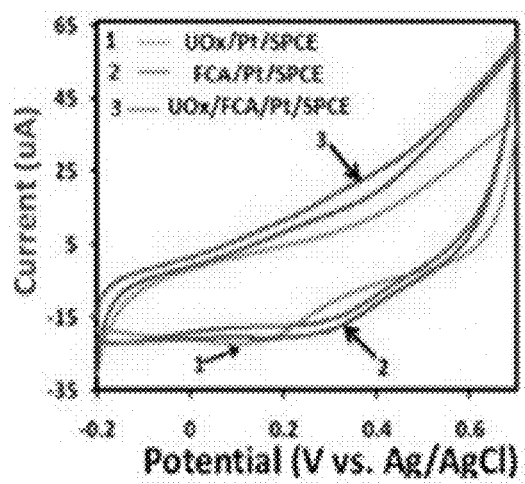 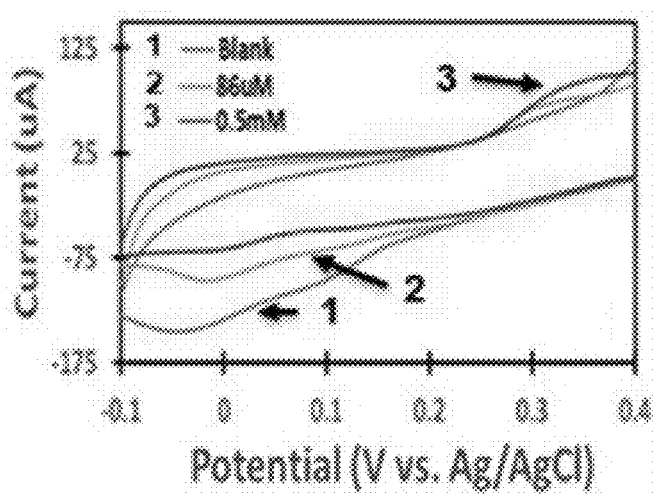
FIG. 16A    FIG. 16B

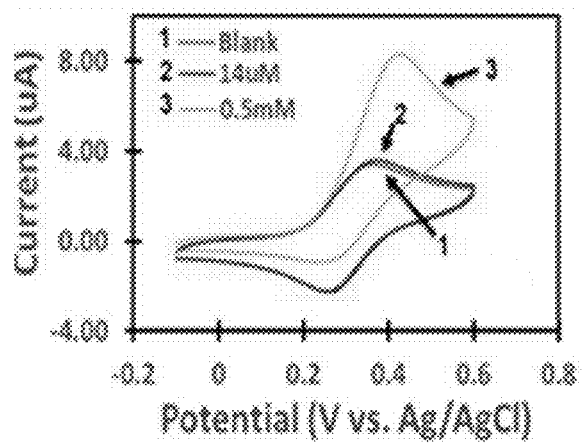 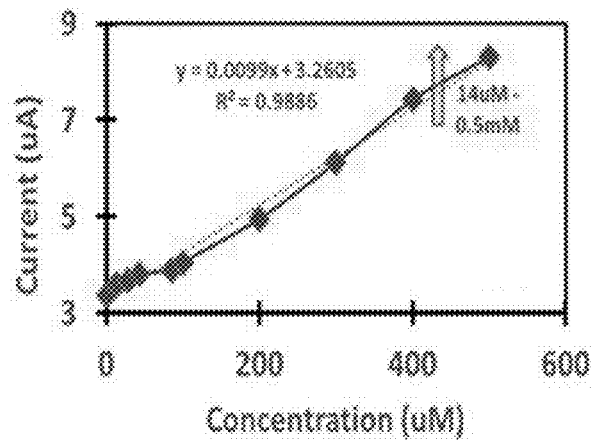
FIG. 17A  FIG. 17B
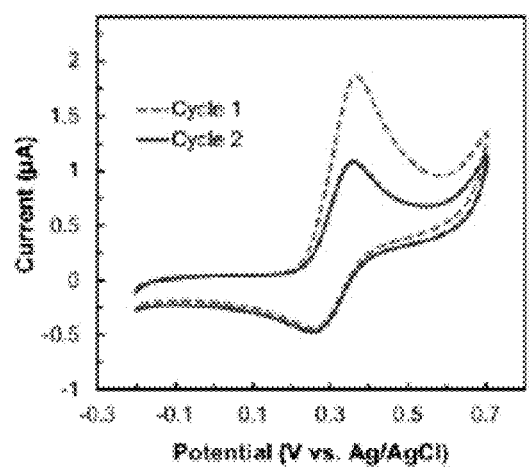
FIG. 18A

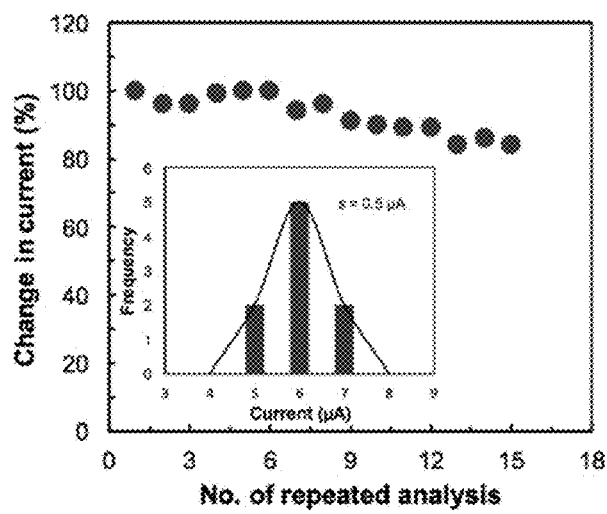
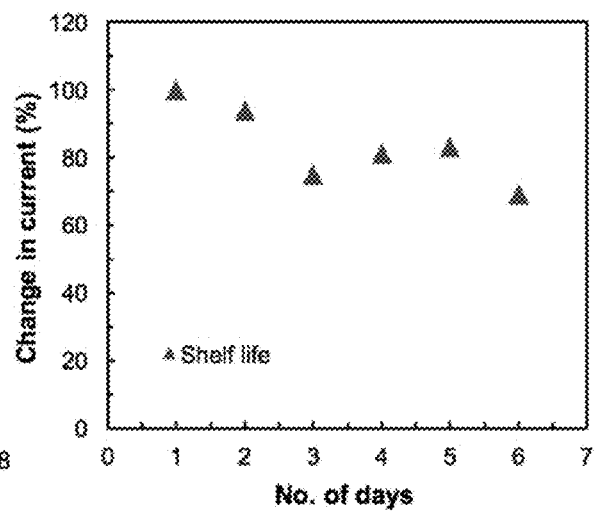
FIG. 23A					FIG. 23B
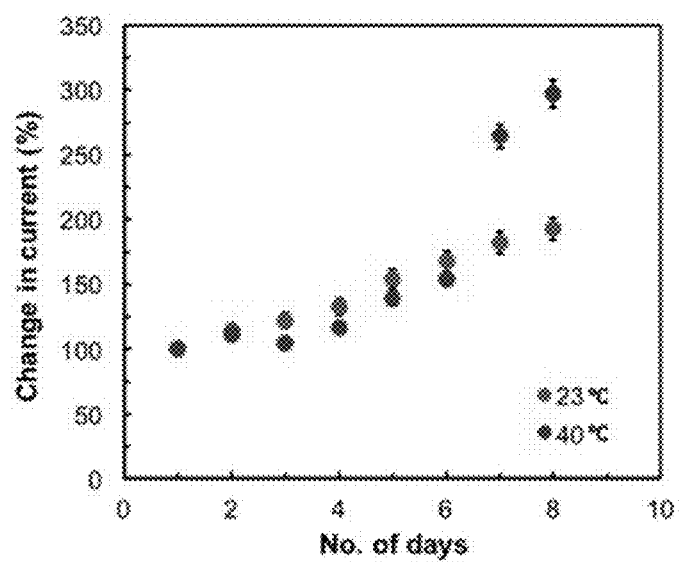
FIG. 23C

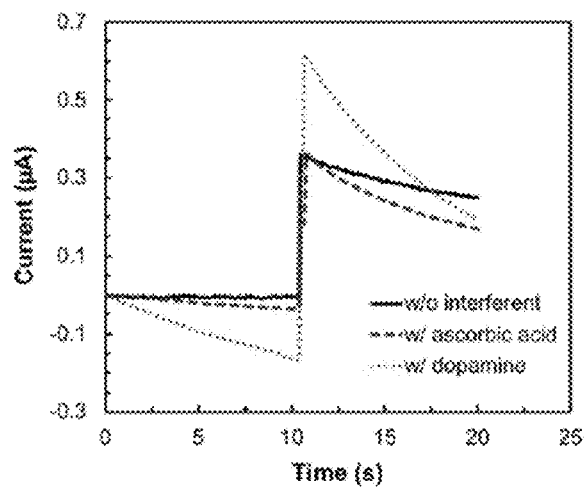
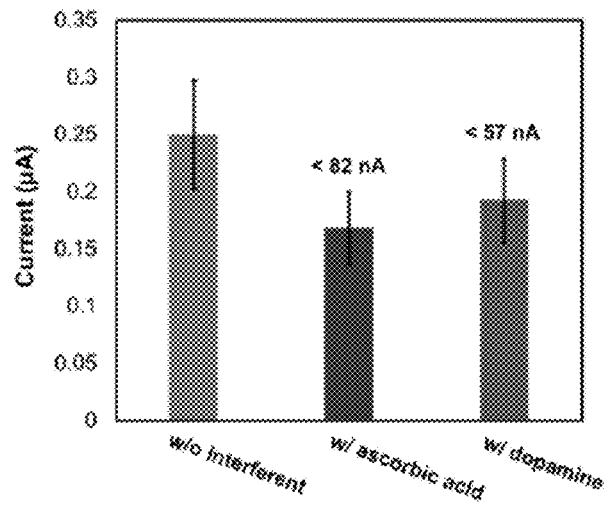
FIG. 24A  FIG. 24B
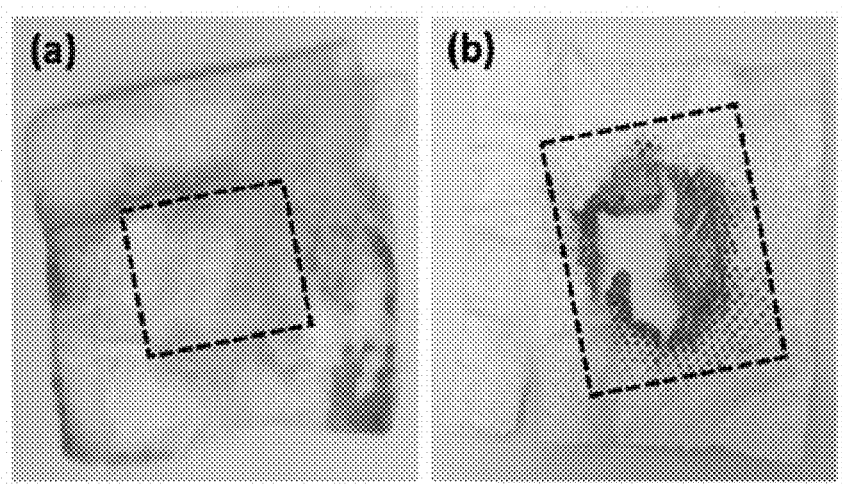
FIG. 25A  FIG. 25B

WOUND MONITORING SENSORS AND USE THEREOF

CROSS-REFERENCE TO A RELATED APPLICATION

This application claims the benefit of U.S. provisional application Ser. No. 62/739,712, filed Oct. 1, 2018, which is incorporated herein by reference in its entirety.

STATEMENT OF GOVERNMENT SUPPORT

This invention was made with government support under Grant No. 1160483 awarded by the National Science Foundation Nanosystems Engineering Research Centre for Advanced Self-Powered Systems of Integrated Biosensors and Technologies (ASSIST). The government has certain rights in the invention.

BACKGROUND

Monitoring the healing of chronic wounds continues to be a challenge in healthcare. Effective non-invasive approaches could facilitate treatment and reduce the adverse outcomes of trauma, surgery, and amputations associated with chronic wounds.

The wound healing process comprises a series of interdependent physiological events that include: (i) homeostasis, (ii) inflammation, (iii) proliferation, and (iv) maturation. Homeostasis occurs in the event of a wound injury, and involves the formation of blood clots with platelets to stop the bleeding. This stage typically lasts from one to three days and it can overlap with the inflammatory phase. The inflammatory phase often lasts from three to twenty days, providing a new framework for blood vessels and cell growth. Inflammatory cells debride injured tissue through increased blood circulation within hours of the occurrence of the injury. The proliferation phase usually lasts from one to six weeks, during which granulation tissue is formed with cells migrating at the wound edges to contract the skin around the damaged area. This allows complete healing with the restoration of underlying tissue.

Existing wound care often entails repeated clinic visits by the patient, throughout the various healing stages of the wound. This is necessary for tracking healing progress and changing of wound dressings.

If the body is unable to heal wounds properly, the patient is at a higher risk of developing localized infections that can lead to systemic infections and traumatic amputations.

Skin ulcers such as diabetic foot ulcers are common wounds that can not only lead to continual breakdown of skin and surrounding tissue, but also increase the risk of deep skin and soft tissue infection. It is more difficult to recognize and monitor the occurrence of a diabetic wound because of a weakened sensory nervous system that does not give normal pain signals.

Internal wounds, in particular, require intensive theranostics, compared to external wounds. Though internal wounds may have an apparent manifestation on the surface, they are associated with causes from within the body and have the potential of recurring.

Conventional approaches to wound assessment are primarily visual. One of the most advanced solutions in practice today involves measurements of wound width and depth through an Aranze Medical monitor that uses a laser for accurate measurements. The optical measurements of changes in size and depth serve as a measure of recovery of injured tissue.

The time between the occurrence of a wound and the beginning of treatment can sometimes be lengthy, which can lead to chronic tissue damage. Even in developed countries, this leads to a more expensive care plan. This necessitates point-of-care techniques to continuously monitor recovery and detect chronicity through rapid analyses. Non-invasive approaches focused on detection and quantification of biomarkers associated with tissue damage and wound healing can facilitate better therapeutic interventions to minimize chronic tissue damage. Such an approach has the potential to personalize therapy to each patient's wound, significantly improving the patient's quality of life while reducing costs of chronic wound care management.

Uric Acid (UA), a metabolic product of purines, is involved in the initiation of inflammatory tissue healing processes. A correlation between UA in the wound fluid and chronic venous leg ulcers has been established. Purine UA levels are elevated in wound fluids with relative concentrations correlating with wound severity.

In humans, systemic UA is the product of purine metabolism. Purines play an important role not only in the formation of nucleic acid precursors, but also in the physiology of cells and platelets. UA is filtered by the kidneys out of the body as a natural waste product. In the case of an injury and cell rupture, UA is formed in the wound (localized UA) from the breakdown of released ATP with metabolites from the tissue. The metabolic reaction of this process converts xanthine to UA, which is then filtered out of the body.

When an injury occurs, fluid oozes in and around a wound through diffusion in the dermal layer of skin and to the surrounding blood vessels. With elevated UA at the site of injury, its vicinity will also have a rise in UA levels. This is also caused by the transport of extracellular fluid by serum in blood vessels, where serum comprises 20% extracellular fluid along with proteins and electrolytes.

In a wound, arginine is another biomarker that is metabolized to urea and ornithine by an enzyme, arginase. This pathway is important in the healing process as it generates nitric oxide, a molecule involved in immune response, proline, a substrate for collagen synthesis, and polyamines, that stimulate cellular proliferation. Due to metabolism, levels of arginine can critically decrease upon injury. To accelerate healing and increase collagen deposition for treatment efficacy, it is necessary to monitor arginine levels and determine personalized therapeutic needs.

Existing wound care sensors are incapable of tracking chronicity from a wound environment. Therefore, there is a need to develop new methods and materials that are non-invasive, can continuously track wood healing in real-time and provide personalized evaluation of wood care.

BRIEF DESCRIPTION OF THE INVENTION

The subject invention provides materials and systems for tracking the chronicity of a wound environment and for continuously monitoring wound healing. The subject invention also provides methods for tracking chronicity of the wound environment, evaluating the severity of a wound and continuously monitoring wound healing.

In one embodiment, the subject invention provides materials and methods for monitoring biomarkers non-invasively from a biofluids (e.g., sweat) in proximity to a wound.

In one embodiment, the subject invention provides a skin-based, non-invasive enzymatic electrochemical biosensors on a wearable platform (such as a sweat patch), which can evaluate the healing of wounds through assessment of biomarker levels. This non-invasive detection from physiologically relevant biofluids reduces or eliminates occlusion effects from, for example, embedding a wound sensor directly in wound fluid.

In one embodiment, the non-invasive wearable sensor system simultaneously measures both a biomarker as well as pH in order to track healing. In accordance with the subject invention, based on correlations of one or more biomarkers and pH of the wound environment with healing, an electrochemical wound sensing system is implemented using the approach of sensor fusion.

This sensor fusion approach (enzymatic+pH sensor) enables calibration of the signal obtained from the sensor on a wound care substrate. In accordance with the teachings provided herein, algorithms can be used for calibrating the system to avoid false readings (positive/negative). This novel approach improves therapeutic efficacy of wound care to the level of point-of-care, thereby reducing the socio-economic costs associated with choric wound.

This technology can be applied to continuously track wound healing progress. The method can comprise a sensor network integrated with low-power electronics on a healing platform of, for example, a bandage or gauze/dressing, to determine healing progress.

In preferred embodiment, the enzymatic electrochemical sensor according to the subject invention comprises an electrode functionalized with an enzyme that oxidizes a biomarker to generate an electrochemical signal. Optionally, the electrode is functionalized with one or more nano-materials. In a specific embodiment, the electrode is screen-printed carbon electrode (SPCE).

The subject invention provides sensor systems that can detect biomarkers related to wound healing (e.g., UA, adenosine, and/or arginine). In a preferred embodiment, this biomarker is UA, as it is established as a primary biomarker for wound healing having elevated levels in chronic wound environments.

To address the issues associated with existing wound care sensors, an enzymatic electrochemical sensor system of the subject invention can be used for precise biomarker detection to track healing on a wound care platform.

In one embodiment, the system utilizes the incorporation of nano-material catalysts for enhanced selectivity and sensitivity through the use of a redox electron shuttle; however, enzymatic approaches can involve challenges relating to enzyme loading and stability, including, for example, denaturation of the involved protein. In one embodiment, enhanced sensor response is achieved through immobilization of the enzyme in an ionic polymer.

In a specific embodiment, Urate oxidase (uricase, UOx) entrapped in a polyvinyl alcohol (PVA)-based cationic polymer forms the sensor, where ferrocene carboxylic acid (FCA) is used as a redox electron shuttle. Different electrochemical techniques (e.g., differential pulse voltammetry (DPV) and cyclic voltammetry (CV)) using UA can be used to investigate and evaluate the functionality of the sensor as a wearable device. The wearable UA biosensor can be used for monitoring healing of chronic wounds non-invasively.

Embedding a biosensor in the wound fluid to monitor biomarkers such as UA can create fouling effects and reduce its capability for continuous tracking. Instead, monitoring systemic UA (or other biomarkers) through sweat in the vicinity of the wound is relatively easy and reduces biosensor occlusion. In one embodiment, the method of the subject invention comprises contacting the wound care sensor with sweat in the vicinity of a wound for monitoring wound healing. This non-invasive approach of the subject invention provides a dressing-embedded biosensor system for use in wound care.

The system facilitates stable and selective detection of biomarkers in rapid wound diagnostics. This technology transforms wound care with efficient and effective wound management on a wearable healing platform. One such example is tracking wounds in diabetics.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-6C show SEM images grown of (6A) Pt nano-flakes; (6B) Ag nano-wires; and (6C) Au nano-particles.

FIG. 7A shows PVA-SbQ interaction with negatively-charged amino acid chains of the UOx enzyme.

FIG. 7B shows structural interactions between the carboxylic functional group of the enzyme and the amine side chains of the polymer.

FIGS. 10A-10E show fluorescence microscopic images of UOx functionalized substrates with various polymer-UOx ratios of (10A) 1:2; (10B) 1:4; (10C) 1:6 and (10D) physisorbed; (10E) depicts a comparison of mean intensities emitted at 570 nm from the UOx substrates.

FIG. 11 shows a plot depicting a comparison of fluorescence intensities emitted from different UOx-loaded substrates at 570 nm. The mean pixel intensities of 1:2, 1:4 and 1:6 polymer-UOx substrates were 1830.89, 742.64 and 440.96 (a.u.) respectively.

FIGS. 12A-12B show SEM micrographs of (12A) physisorbed and (12B) UOx functionalized substrates at 100 nm.

FIG. 13A shows a Nyquist plot showing the variation of impedance in the presence of FCA at 0.3 V between 1 mHz to 100 kHz on functionalized substrates with varied loading.

FIG. 13B shows a plot depicting the change in UOx activity and current density with varied UOx loading.

FIG. 14 shows a bode plot showing the variation in impedance magnitude and phase angle on different UOx-loaded substrates with frequency from 0.001 Hz to 100 kHz at 0.3 V.

FIG. 15 shows CV of Ag nanowire modified SPCE in PBS in the absence of $H_2O_2$ (curve 1); and 0.1 M $H_2O_2$ (curve 2) at a scan rate of 20 mV $s^{-1}$.

FIGS. 16A-16B show CV responses of (16A) Pt nanoflakes modified UOx-Pt-SPCE (curve 1), FCA-Pt-SPCE (curve 2) and, UOx-FCA-Pt-SPCE (curve 3) in the presence of 48 μM UA; (16B) Ag nano-wires modified UOx-Ag-SPCE in 0.02 M PBS in the absence of UA (curve 1), 86 μM UA (curve 2), and 0.5 mM UA (curve 3).

FIG. 17A shows Au nano-dots modified UOx-Au-SPCE in PBS in the absence of UA (curve 1), 14 μM UA (curve 2), and 0.5 mM UA (curve 3) measured at a scan rate of 20 mV $s^{-1}$.

FIG. 17B shows a linear response of Au nano-material modified UOx-Au-SPCE with increasing UA concentrations from 14 μM to 0.5 mM measured at a scan rate of 20 mV $s^{-1}$.

FIGS. 18A-18D show (18A) CV response of UOx entrapped electrode in the presence of 20 mM FCA, showing Cycles 1 and 2 with oxidation peak potential, Epa=0.4 V; (18B) reaction mechanism depicting inhibition of $O_2$ in its absence and presence, and its effect on FCA signal (Epa=0.45 V); (18C) electron transfer mechanism depicting inhibition of 1 mM $H_2O_2$ in the absence and presence of horseradish peroxidase (HRP), and its effect on FCA signal; (18D) concentration of $H_2O_2$ in presence and absence FCA, measured by $H_2O_2$ assay. All the above CV measurements were carried out at 20 mV $s^{-1}$.

FIGS. 23A-23C show: (23A) a representing repeatability of the enzymatic electrode obtained through repeated measurements of 48 μM uric acid. The inset is the distribution curve representing reproducibility obtained from nine different electrodes measured at the same condition; (23B) a representing shelf life of the enzymatic electrodes, where the measurements were carried out in 48 μM UA; (23C) a depicting comparison of response of entrapped UOx under physiological conditions over a week.

FIGS. 24A-24B show: (24A) amperometric signal of UA (100 μM) in the absence and presence of ascorbic acid (100 μM) and dopamine (100 μM); (24B) a chart representing the reduction in current in presence and absence of ascorbic acid and dopamine at 20 s.

FIGS. 25A-25D show wound dressings from patients from the wound clinic. The marked lines represent the extraction area.

DETAILED DESCRIPTION OF THE INVENTION

The subject invention provides materials and systems for tracking the chronicity of a wound environment and for continuously monitoring wound healing. The subject invention also provides methods for tracking chronicity of the wound environment, evaluating the severity of a wound and for continuously monitoring wound healing.

The subject invention provides point-of-care techniques, which entail the sensing of one or more biomarkers associated with wound healing, the continuous monitoring of the recovery progress, and the detection of chronicity through rapid analyses.

In one embodiment, the subjection invention provides a non-invasive method to track the healing of a wound using electrochemical biosensing. This method offers many benefits, including shorter hospitalization time, prevention of amputation, and an improved understanding of the recovery processes. Electrochemical biosensing provides a cost-effective alternative with greater simplicity and improved sensitivity. Also, the methods according to the subject invention are able to continuously measure the biochemical changes occurring in the wound in real time.

In certain embodiments, the wound may be an internal wound or an external wound on the skin. In a specific embodiment, the wound is a skin ulcer. The skin ulcer may be located, for example, on the foot, hand, leg, arm, face, and/or torso.

In a preferred embodiment, the subject invention utilizes an enzymatic electrochemical biosensor for monitoring the healing of wounds. This approach allows patients and healthcare providers to continuously monitor wounds and examine severity and chronicity for formulating effective wound management strategies and assessing therapeutic efficacy. This also allows earlier intervention to improve recovery prior to permanent tissue damage.

Figure 1A:
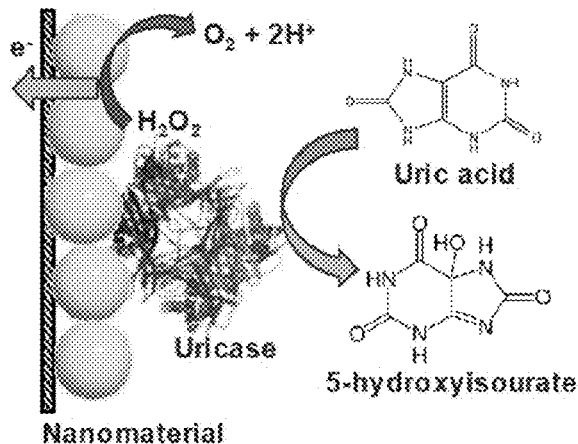
FIGS. 1A-1C show enzymatic transducers for monitoring wound healing and severity.
Figure 1B:
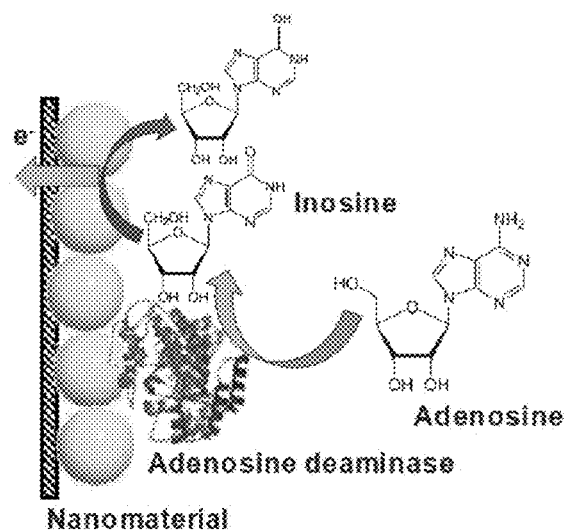

In one embodiment, the subject invention provides a sensor system that can detect one ore more biomarkers related to wound healing (e.g., UA, adenosine, and/or arginine) (FIG. 1). UA is one of the primary biomarkers for wound healing, as it shows elevated levels in chronic wound environments.

In one embodiment, the subject invention provides an enzymatic electrochemical sensor system on a wound care platform for precise biomarker detection to track wound healing. In one embodiment, the system incorporates nano-material catalysts for enhanced selectivity and sensitivity through the use of an electron transfer mediator.

In one embodiment, the enzymatic electrochemical sensor for detecting a biomarker in wound healing comprises an electrode functionalized with an enzyme that oxidizes the biomarker to generate an electrochemical signal. Optionally, the electrode can be functionalized with one or more nano-materials.

In one embodiment, the enzymatic electrochemical sensor comprises one or more electrodes and, optionally, an electron transfer mediator. The electrodes typically include a working electrode, a reference electrode and a counter electrode. The working electrode can be made of, for example, gold, silver, copper, platinum or carbon. Preferably, the reference electrode is Ag/AgCl electrode and the counter electrode is made of platinum or carbon. In a specific embodiment, the working electrode is a screen-printed carbon electrode (SPCE).

In a further embodiment, the three electrodes are assembled so that the reference and counter electrodes are placed on the surface of an SPCE. In another embodiment, the one or more electrodes may be a plate, rod, or wire. In a specific embodiment, the electrodes are planar electrodes.

In one embodiment, the working electrode is modified or functionalized by an enzyme that catalyzes one or more biomarkers related to wound healing. The working electrode may also be functionalized with one or more nano-materials. In enzyme electro-chemistry, the immobilization technique determines enzyme loading and stability on the surface of the electrode. Immobilization methods include, for example, physisorption, chemisorption, and entrapment. In one embodiment, the enzyme is immobilized on the surface of the working electrode by physisorption or by entrapment in a polymer matrix coated on the surface of the working electrode.

Enzymes (for example, uricase, adenosine deaminase, arginase and xanthine oxidase (XO)) are known to be selective to their specific biochemical pathways. However, all enzymes for UA do not undergo direct electron transfer on the working electrode for specific detection. Thus, detection of their by-products can be used. For example, the oxidation of UA yields hydrogen peroxide ($H_2O_2$) as a by-product (FIG. 1a), which can be detected.

Dissolved oxygen can interfere with peroxide reduction signal. To eliminate this interference, nano-materials, such as metal catalysts, can be incorporated into the system of the subject invention to facilitate specific detection. This reduces interference and facilitates monitoring oxidation of $H_2O_2$ at a different potential, addressing selectivity issues in existing sensors.

Enzymatic approaches can create challenges of controlled enzyme loading and stability associated with denaturation of the protein. Also, enzymes are known for their sensitivity to pH and temperature. pH is thus critical to retain activity and reduce denaturation issues. This can be addressed with enzyme entrapment in an ionic polymer matrix.

In one embodiment, an enhanced sensor response is achieved through immobilization of the enzyme in an ionic polymer, such as Poly (vinyl alcohol) N-methyl-4(4'-formylstyryl)-pyridinium-metho-sulfate-acetal (PVA-SbQ). The ionic functional groups of the polymer provide robust electrostatic interactions to attach and hold the enzyme on the electrode surface. Its freestanding chains interact with the π-conjugative structure on the electrodes (e.g., planar transducer) through π-π hydrophobic interaction. This, along with the incorporation of nano-materials enhances enzyme loading with maximum utilization of the working electrode area. The enhanced enzyme stability assists in continuous detection of the biomarkers.

In one embodiment, the enzyme, e.g., uricase (UOx), adenosine deaminase, arginase, and/or XO may be entrapped or encapsulated in matrices of other polymers such as PANI, polypyrrole and PVC, or in gels such as chitosan, silica and collagen.

In one embodiment, the enzyme is entrapped in the polymer with a polymer to enzyme ratio (v/v) of from 10:1 to 1:20, from 5:1 to 1:10, from 2:1 to 1:6, from 1:1 to 1:6, or from 1:2 to 1:6. The enzyme is entrapped in the polymer with a polymer to enzyme ratio (v/v) of, for example, 5:1, 4:1, 3:1, 2:1, 1:1, 1:2, 1:3, 1:4, 1:5, 1:6, 1:7, 1:8, 1:9, or 1:10. In a preferred embodiment, the enzyme is entrapped in the polymer with a polymer to enzyme ratio (v/v) of 1:2, 1:4 or 1:6, more preferably, 1:2.

Various metal nano-materials can be used for enzymatic detection of biomarkers (e.g., UA) in wound healing. In one embodiment, the nano-materials may be metal catalysts, nano-structures and/or a combination thereof. The metal catalysts can be used to functionalize the electrode. These metal catalysts include, for example, copper (Cu), zinc (Zn), silver (Ag), gold (Au), platinum (Pt) and carbon (C). The metal catalysts may be deposited on the working electrode as, for example, nanoparticles, nano-flakes, nano-rods, nano-wires or nano-dots, preferably, Pt nano-flakes, Ag nanowires or Au nano-dots.

In one embodiment, the metal catalysts may be deposited with a size/length of from about 10 nm to 1000 nm, about 10 nm to 900 nm, about 10 nm to 800 nm, about 10 nm to 700 nm, about 10 nm to 600 nm, about 10 nm to 500 nm, about 10 nm to 450 nm, about 10 nm to 400 nm, about 10 nm to 350 nm, about 10 nm to 300 nm, about 10 nm to 250 nm, about 20 nm to 250 nm, about 30 nm to 250 nm, about 40 nm to 250 nm, about 50 nm to 250 nm, about 60 nm to 250 nm, about 70 nm to 250 nm, about 80 nm to 250 nm, about 90 nm to 250 nm, about 100 nm to 250 nm, about 150 nm to 250 nm, about 200 nm to 250 nm, about 220 nm to 300 nm, about 250 nm to 300 nm, about 250 nm to 280 nm, about 250 nm to 260 mm, about 10 nm to 200 nm, about 10 nm to 150 nm, about 10 nm to 100 nm, about 10 nm to 90 nm, about 10 nm to 80 nm, about 10 nm to 70 nm, about 10 nm to 60 nm, about 10 nm to 50 nm, about 10 nm to 40 nm, about 10 nm to 30 nm, about 20 nm to 200 nm, about 20 nm to 100 nm, about 30 nm to 100 nm, or about 40 nm to 80 nm.

In a further embodiment, the metal catalysts may be deposited as nano-flakes having a thickness in the range of from about 2 nm to 100 nm, about 5 nm to 90 nm, about 10 nm to 80 nm, about 10 nm to 70 nm, about 10 nm to 60 nm, about 15 nm to 50 nm, about 20 nm to 50 nm, about 25 nm to 40 nm, or about 25 nm to 30 nm.

Nano-structures such as carbon nanotubes (CNTs), e.g., multi-walled carbon nanotubes (MWCNTs), may also be used due to their catalytic activity in the electrochemical reaction. In a specific embodiment, the nano-material comprises MWCNTs and/or Au. Nano-materials of carbon and gold provide superior performance owing to greater conductivity and catalytic activity. The advantages include increased electrode surface area, fast electron transfer, and improved surface-confined reactions. Carbon nanotubes have open-end structures with an edge plane of highly ordered pyrolytic graphite. The walls of multi-walled carbon nanotubes (MWNT) with large basal planes are highly conductive while the edges hold high capacitive and electrocatalytic properties.

In one embodiment, CNTs may have a length ranging from about 100 nm to 2 mm, from about 100 nm to 1.5 mm, from about 100 nm to 1.2 mm, from about 200 nm to 1 mm, from about 200 nm to 900 µm, from about 200 nm to 800 µm, from about 200 nm to 700 µm, from about 200 nm to 600 µm, from about 200 nm to 500 µm, from about 200 nm to 400 µm, from about 200 nm to 300 µm, from about 200 nm to 200 µm, from about 300 nm to 200 µm, from about 400 nm to 200 µm, from about 500 nm to 200 µm, from about 500 nm to 100 µm, from about 500 nm to 90 µm, from about 500 nm to 80 µm, from about 500 nm to 70 µm, from about 500 nm to 60 µm, from about 500 nm to 50 µm, from about 500 nm to 40 µm, from about 500 nm to 30 µm, from about 500 nm to 20 µm, from about 500 nm to 10 µm, from about 800 nm to 10 µm, from about 1 µm to 20 µm, from about 2 µm to 20 µm, from about 1 µm to 10 µm, or from about 2 µm to 10 µm.

In one embodiment, MWCNTs may have from about 2 to 200 layers/walls, from about 2 to 150 layers/walls, from about 2 to 120 layers/walls, from about 2 to 100 layers/walls, from about 3 to 100 layers/walls, from about 4 to 100 layers/walls, from about 5 to 100 layers/walls, from about 5 to 90 layers/walls, from about 5 to 80 layers/walls, from about 5 to 70 layers/walls, from about 5 to 70 layers/walls, from about 5 to 60 layers/walls, from about 5 to 50 layers/walls, from about 5 to 40 layers/walls, from about 5 to 30 layers/walls, from about 5 to 20 layers/walls, or from about 5 to 10 layers/walls.

In one embodiment, the enzymatic electrochemical sensor further comprises an electron transfer mediator. The electron transfer mediator provides improved response from the reaction on the transducer (e.g., electrodes). The electron transfer mediator may be a redox electron shuttle, which facilitates improved electron transport between the active site of the enzyme and the electrode. The electron transfer mediators include, but are not limited to, derivatives of benzoquinone, ferricene/ferrocene and methyl/methoxy compounds. Ferri/ferro based compounds require lower energy for the redox reaction, enabling detection in a lower potential window with minimized interference from other electro-active species. For example, ferrocene and its derivatives (ferricinium ion forms) can be electron acceptors for specific enzymes and molecules.

In one embodiment, the electron transfer mediator comprises a redox electron shuttle. In a specific embodiment, the redox electron shuttle is ferrocene carboxylic acid (FCA). Other redox electron shuttles (e.g., prussian blue, methylene blue, congo red, etc.) can also be used for enhanced sensitivity. Advantageously, the enzymatic electrochemical sensor of the subject invention addresses the limited diffusion rates seen in other biosensors, providing improved signal with minimized interference from dissolved oxygen in generated hydrogen peroxide.

In one embodiment, the enzymatic electrochemical sensor has a detection range of from about 0.1 nM to about 10 mM, from about 0.1 nM to about 9 mM, from about 0.1 nM to about 8 mM, from about 0.1 nM to about 7.3 mM, from about 0.1 nM to about 6 mM, from about 0.1 nM to about 5 mM, from about 0.1 nM to about 4 mM, from about 0.1 nM to about 3 mM, from about 0.1 nM to about 2 mM, from about 0.1 nM to about 1 mM, from about 1 nM to about 1 mM, from about 10 nM to about 1 mM, from about 50 nM to about 1 mM, from about 100 nM to about 1 mM, from about 200 nM to about 1 mM, from about 500 nM to about 1 mM, from about 1 µM to about 500 µM, from about 5 µM to about 300 µM, from about 10 µM to about 300 µM, from about 12 µM to about 300 µM, or from about 12 µM to about 100 µM.

In specific embodiments, the enzymatic electrochemical sensor using UOx has a detection range of from about 12 µM to about 100 µM. The enzymatic electrochemical sensor using UOx has a detection limit of about 12 µM or less. The enzymatic electrochemical sensor using XO has a detection range of from about 0.1 nM to about 7.3 mM. The enzymatic electrochemical sensor using XO has a detection limit of 0.1 nM or less.

In one embodiment, the subject invention provides an electrochemical wound sensor system comprising an enzymatic electrochemical sensor on a wound care platform. The wound care platform can comprise a flexible fabric-based material, such as poly-dimethyl-siloxane sheet, adhesive vinyl sheet, bandage, patch, gauze, and dressing materials.

In accordance with the subject invention, based on correlations of the biomarker and pH of the wound environment with healing, an electrochemical wound sensing system is implemented using the approach of sensor-fusion (enzymatic+pH sensor). The sensor fusion approach enables calibration of the signal obtained from the sensor on a wound healing platform, based on the correlations of pH and the concentration of one or more biomarkers, e.g., UA, with healing.

In one embodiment, the electrochemical wound sensor system of the subject invention is wearable. Preferably, this non-invasive wearable sensor system simultaneously measures both a biomarker as well as the pH, in order to track healing. This sensor-fusion approach enables calibration of the signal obtained from the sensor on a wound care substrate. In accordance with the teachings provided herein, algorithms can be built for calibration of the system to avoid false readings (positive/negative). This novel approach improves therapeutic efficacy of wound care to the level of point-of-care, reducing the associated socio-economic costs.

In one embodiment, the electrochemical wound sensor of the subject invention has a long shelf life. In another embodiment, the electrochemical wound sensor of the subject invention is reusable and reproducible. Repeatability and reproducibility of this biosensor can result in stable response over a day with multiple uses.

In one embodiment, the electrochemical wound sensor of the subject invention has a stability of about 1 to about 20 days, about 1 to about 18 days, about 3 to 15 days, about 4 to 12 days, about 5 to 10 days, or about 6 to 9 days, at 40° C. The electrochemical wound sensor of the subject invention has a stability of about 2 to about 100 days, about 3 to 90 days, about 4 to 80 days, about 5 to 70 days, about 6 to 60 days, about 7 to 50 days, about 8 to 40 days, about 9 to 30 days, about 10 to 20 days or about 10 to 15 days at room temperature.

In a further embodiment, the electrochemical wound sensor of the subject invention has a stability of at least about 2, 3, 4, 5, 6, 7, 8, 9, or 10 days, at 40° C. In a preferred embodiment, the electrochemical wound sensor of the subject invention has a stability of about 7 days, at 40° C.

In another embodiment, the electrochemical wound sensor of the subject invention has a stability of at least about 2, 3, 4, 5, 6, 7, 8; 9, 10, 11, 12, 13, 14, 15, 16, 17, 18, 19, 20, 21, 22, 23, 24, 25, 26, 27, 28, 29, or 30 days at room temperature. In a preferred embodiment, the electrochemical wound sensor of the subject invention has a stability of about 15 days at room temperature.

In one embodiment, the subject invention provides a wearable wound sensor comprising a flexible substrate integrated on a fabric-based material, the flexible substrate comprising one or more electrodes, and optionally, an electrode transfer mediator, wherein one or more electrodes are functionalized with one or more enzymes, e.g., uricase, adenosine deaminase, arginase and/or XO on the surfaces. In a further embodiment, the enzyme may be entrapped in polymer such as PVA-SbQ. The one or more electrodes can be further deposited with metal nanomaterials such as metal catalysts and/or nano-structures.

In one embodiment, the subject invention provides a wearable wound sensor comprising a flexible substrate integrated on a fabric-based material, the flexible substrate comprising a working electrode, a reference electrode, a counter electrode, and optionally, an electrode transfer mediator, wherein the working electrode is functionalized with an enzyme, e.g., uricase, adenosine deaminase, arginase and/or XO on the surface of the electrode. In a further embodiment, uricase is entrapped in a PVA-SbQ polymer matrix while XO is functionalized on the surface of the working electrode deposited with nano-materials comprising MWCNTs and/or Au. In a specific embodiment, the electrode transfer mediator comprises FCA and the working electrode is a carbon electrode.

In a preferred embodiment, the wearable wound sensor comprises a flexible substrate integrated on a fabric-based material, the flexible substrate comprising a working electrode, a reference electrode, a counter electrode, and an electrode transfer mediator being FCA, wherein the working electrode is functionalized with uricase on the surface of the electrode, wherein the uricase is entrapped in a PVA-SbQ polymer matrix and the working electrode is a carbon electrode, for example, SPCE.

In a specific embodiment, the wearable wound sensor comprises a flexible substrate integrated on a fabric-based material, the flexible substrate comprising a working electrode, a reference electrode, a counter electrode, wherein the working electrode is functionalized with XO on the surface of the working electrode deposited with nano-materials comprising MWCNTs and/or Au, and the working electrode is a carbon electrode (e.g., graphite).

In a specific embodiment, the wound care substrate is a sweat patch that is wearable on the skin of a subject. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the subject invention provides materials and methods for monitoring one or more biomarkers non-invasively from sweat in the proximity of a wound, including in the presence of other physiological fluids. Skin-based, non-invasive enzymatic electrochemical biosensor on a wearable platform (such as a sweat patch) can improve and/or evaluate the healing of internal wounds through assessment of biomarker levels. This non-invasive detection from physiologically-relevant biofluids reduces or eliminates occlusion effects from, for example, embedding a wound sensor directly in wound fluid.

Figure 2A:
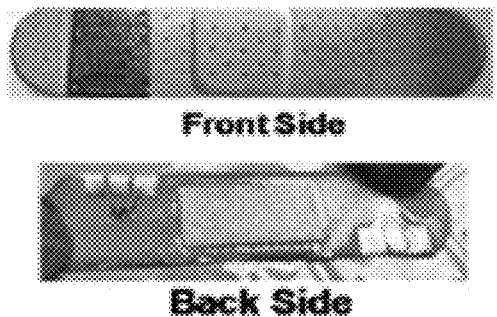
FIG. 2A shows a wearable wound sensor integrated with miniaturized electronics on a bandage.
Figure 2B:
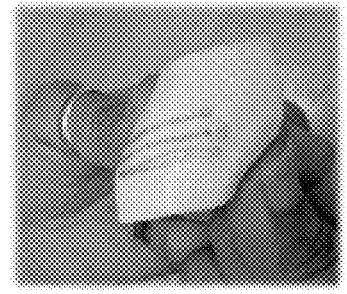
FIG. 2B shows a flexible wound care sensor on dressing material.
Figure 3A:
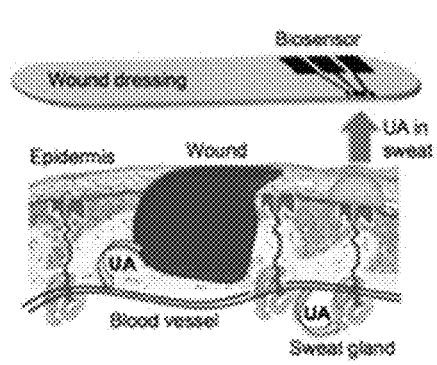
FIG. 3A shows a schematic of an electrochemical wound care biosensor for monitoring UA through sweat at the vicinity of the wound.
Figure 3B:
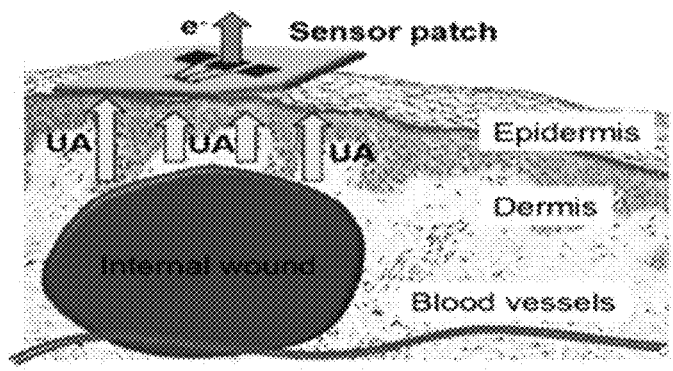
FIG. 3B shows a schematic of a non-invasive sensor patch to monitor wound healing.

In one embodiment, the substrate is based on a flexible fabric-based material such as gauze, bandages, or dressing materials. Fabrication of the sensor system on such 3D material can involve metal deposition, photolithography and/or etching techniques. Miniaturized electronics for implementing wireless functionality of the sensor has been achieved (FIG. 2). In one embodiment, the wound care sensor is flexible and can be integrated on dressing materials. In a specific embodiment, the wearable wound sensor is integrated with miniaturized electronics on a bandage (FIG. 2). In another embodiment, the wearable wound sensor is integrated in a patch applied on the skin to monitor wound healing (FIG. 3).

In one embodiment, the subject invention provides methods for monitoring wound healing of a subject comprising contacting a wound care substrate with a wound, the wound care substrate comprising an enzymatic electrochemical sensor of the subject invention; and measuring an electrical signal or measuring a change in the electrical signal. The electrical signal is generated from a reaction between the enzymatic electrochemical sensor and a biomarker in the wound. In one embodiment, the electrical signal is a current or voltage that can be measured using CV or DPV.

In one embodiment, the electrical signal is indicative of the presence of one or more biomarkers related to wound healing. The method can also be used to measure the concentration of the biomarkers in the wound or biofluid of the wound, the biofluid being present at the wound or in the vicinity of the wound. The change in the electrical signal is indicative of the change in concentrations of the biomarker related to wound healing. In specific embodiments, a decrease in the electrical signal is indicative of the healing of the wound while an increase in the electrical signal is indicative of the aggravation of the wound.

In a further embodiment, the method further comprises detecting the level/concentration of a biomarker, e.g., UA, adenosine, arginine and/or xanthine, in the wound or biofluid. Detecting the level/concentration of the biomarker in the wound or biofluid may comprise comparing the measured signal with a standard curve. Moreover, the method can further comprise detecting the pH of the wound or biofluid. Detecting the pH of the wound or biofluid may comprise comparing the measured signal with a standard curve.

In one embodiment, the subject invention provides methods for assessing the severity of a wound in a subject comprising contacting a wound care substrate with the wound or biofluid, the wound care substrate comprising an enzymatic electrochemical sensor of the subjection invention; and measuring an electrical signal generated from a reaction between the enzymatic electrochemical sensor and a biomarker in the wound, or a change in the electrical signal.

In one embodiment, contacting a wound care substrate with a wound may comprise applying the wound care substrate onto the wound, applying the wound care substrate in the vicinity of the wound, embedding the wound care substrate in the wound, contacting the wound care substrate with a biofluid of the wound, contacting the wound care substrate with a wound extract, embedding the wound care substrate in the wound extract, and/or embedding the wound care substrate in the biofluid of the wound, wherein the biofluid of the wound is present at the wound or in the vicinity of the wound. In specific embodiments, the biofluid is sweat, plasma, blood, urine, tear, saliva, or serum.

In one embodiment, the vicinity of a wound includes the area near or surrounding the wound, having a distance to the wound. The distance may be from about 0.1 mm to 50 cm, from about 0.5 mm to 30 cm, from about 1 mm to 20 cm, from about 1 mm to 15 cm, from about 1 mm to 10 cm, from about 1 mm to 5 cm, from about 1 mm to 4 cm, from about 1 mm to 3 cm, from about 1 mm to 2 cm, from about 1 mm to 1 cm, from about 2 mm to 15 cm, from about 3 mm to 15 cm, from about 4 mm to 15 cm, from about 5 mm to 15 cm, from about 1 cm to 12 cm, from about 2 cm to 12 cm, from about 3 cm to 10 cm, from about 4 cm to 10 cm, or from about 5 cm to 10 cm.

The biosensors of the subject invention can be applied to both acute and chronic wounds. In the case of an injury and cell rupture, UA is formed in the wound (localized UA) from the breakdown of released ATP with metabolites from the tissue. The metabolic reaction of this process converts xanthine to UA, which is then filtered out of the body. When an injury occurs, fluid oozes in and around a wound through diffusion in the dermal layer of skin and to the surrounding blood vessels (FIG. 3). With elevated UA at the wound, its vicinity also has a rise in UA levels. This is also caused by the transport of extracellular fluid by serum in blood vessels, where serum typically comprises 20% extracellular fluid along with proteins and electrolytes. The amount of UA found in the serum of patients with chronic wounds typically spikes up from a normal range of for example, 140-480 mM to 245-780 mM.

Sweat, reported to have ~24.5 µM UA, which is typically 6.3% of that in serum, can be used to perform clinical studies for systemic uric acid detection based on a correlation of its elevated levels in serum for non-healing wounds. Due to the osmotic gradients, metabolites, and components in the blood vessels in/near the wound, diffuse into the sweat glands and surrounding tissues (FIG. 3). Hence, continuous monitoring of biomarkers such as UA through the sweat in the wound area can assist to assess its healing.

In one embodiment, the sensing system and methods of the subject invention allow the detection of the analyte/biomarker from a very low volume of sample, e.g., sweat. In specific embodiments, the volume of the sample is at least about 1 µL, 10 µL, 20 µL, 50 µL, 100 µL, 200 µL, 500 µL, 1000 µL, 2 mL, 5 mL, 10 mL, 15 mL, 20 mL, or 25 mL. In other embodiments, the volume of the sample is from about 1 µL to about 100 mL, from about 10 µL to about 50 mL, from about 20 µL to about 20 mL, from about 50 µL to about 10 mL, from about 100 µL to about 5 mL, from about 200 µL to about 2 mL, or from about 500 µL to about 1000 µL.

In a further embodiment, the volume of the sample is from about 1 µL to about 1 mL, from about 1 µL to about 800 µL, from about 1 µL to about 500 µL, from about 1 µL to about 400 ML, from about 1 µL to about 300 µL, from about 1 µL to about 200 µL, from about 1 µL to about 100 µL, from about 1 µL to about 80 µL, from about 1 µL to about 70 µL, from about 1 µL to about 60 µL, from about 1 µL to about 50 µL, from about 1 µL to about 40 µL, from about 1 µL to about 30 µL, from about 1 µL to about 20 µL, or from about 1 µL to about 10 µL.

In one embodiment, the subject invention provides methods for monitoring wound healing by detecting UA in or around the wound. UA is the product of purine metabolism in humans. The levels of UA in human blood show substantial increase at the time of wound formation with relative concentrations correlating with wound severity. These elevated levels can be attributed to cell breakdown at a wound site.

UA is also known to be involved in the initiation of inflammatory tissue healing. Hence, UA is considered a highly specific indicator of wound status and infection. UA measured from a wound environment can provide a comprehensive understanding of injured tissue recuperation and lesion healing. Other techniques for UA detection involve potentiometric, amperometric, optical and conductometric approaches.

Figure 4:
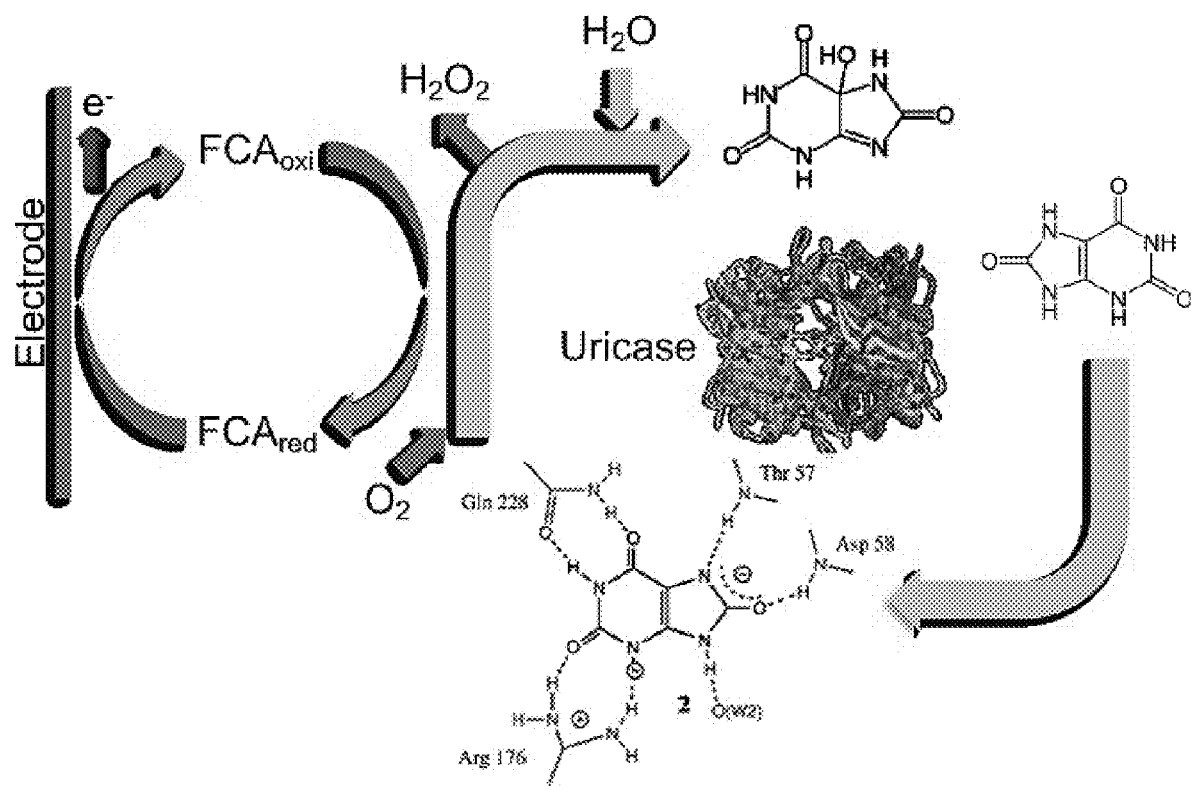
FIG. 4 shows a schematic representation of the uric acid oxidation by UOx and oxidation of $H_2O_2$ via mediated electron transfer using ferrocene carboxylic acid (FCA) as a redox shuttle.

The reaction mechanism of enzymatic UA oxidation in UOx is illustrated in FIG. 4. The enzyme UOx converts UA ($C_5H_4N_4O_3$) to 5-hydroxyisourate ($C_5H_4N_4O_4$) through oxidation (Eq. 1). The formed 5-hydroxyisourate further reacts with water to produce carbon dioxide and allantoin ($C_4H_6N_4O_3$) (Eq. 2). The byproduct ($H_2O_2$) from this reaction is further oxidized in the presence of FCA to generate an electric signal. Thus, the assessment of wound healing through monitoring UA can be performed by monitoring $H_2O_2$ oxidation.

The use of an enzyme, e.g., urate oxidase/uricase (UOx), in the subject methods, facilitates for specific detection of an analyte. In such cases, the enzyme-functionalized substrates are prepared by careful immobilization of the enzyme on the electrode surface through various immobilization techniques, which provides a platform for the enzymatic reaction and assists in maintaining the enzyme activity over time.

These methods include adsorption and entrapment of the enzyme within a polymer (polyaniline/polypyrrole/polyvinyl chloride) based matrix on a carbon material (screen printed/glassy carbon). Other methods include the entrapment or encapsulation of the enzyme in a polymer or gel (silica/collagen/chitosan), which enhances ionic interactions between the enzyme and the transducer. Entrapped immobilization provides strong electrostatic interactions between the enzyme and the polymer on the working electrode, with minimum conformational change. This reduces the likelihood of leaching that could lead to enzyme degradation and loss in activity. These matrices not only bind with the enzyme through strong covalent bonds, but also protect the electrode surface from fouling and assist in specific detection.

In one embodiment, the subject invention provides a nano-material based biosensor for continuous monitoring of UA with improved sensitivity and a lower detection limit within the physiologically relevant range of a wound. Specifically, PVA-SbQ entrapped UOx enzymatic reaction can be utilized to determine UA concentration in, for example, sweat samples. PVA-SbQ, a stable, cationic polymer, provides a strong support to the enzyme while maintaining its activity over the duration of analysis. This polymer has not been extensively used in electrochemical applications due to its limitation of ionic diffusion from a bulk electrolyte on crosslinking. However, instead of crosslinking and utilizing its hydrophobic interactions, enzyme activity can be maintained by retaining its cationic property, which also helps in guiding the orientation of the enzyme. Its protective effect provides the advantage of biosensors having a longer lifetime.

Biocompatible metal nano-materials of Au and Ag provide enhanced signal as compared to Pt nanoparticles with higher current. The nano-enzymatic electrode provides the capability to monitor the byproduct of the enzymatic reaction with the help of electron shuttle probe, e.g., FCA. FCA enables electron transfer with enhanced response, without interference from oxygen. Locating this enzymatic electrode in the wound and/or its vicinity enables continuous monitoring of changes in biomarker (e.g., UA) levels.

In a specific embodiment, the enzymatic electrochemical sensor for continuous monitoring of UA is fabricated by entrapping UOx in a stable cationic polymer nano-material modified SPCE, the nano-material being Pt nano-flakes, Ag nanowires and/or Au nano-dots. Among the different nano-materials explored, the globular morphology of the Au nano-particles' assisted in improved detection with comparatively superior response over a wider physiological range. This structure provide greater enzyme loading with larger surface area for enzyme binding.

In one embodiment, the subject invention provides methods for monitoring the wound healing by detecting xanthine in the wound. XO, the enzyme responsible for oxidation of xanthine in purine metabolism allows xanthine to be used as a biomarker in wound diagnostics.

Breakdown of xanthine in purine metabolism is quick, and its conversion to UA is almost immediate in the purine metabolic pathway. The enzyme XO catalyzes oxidation of xanthine to UA with hydrogen peroxide as a byproduct. Utilization of this enzymatic reaction and monitoring its byproduct formation in wound dressings enables continuous monitoring of changes in xanthine levels. Manipulating this enzymatic reaction on the transducer surface with a nano-material enzyme matrix assists in rapid detection and enhanced sensitivity.

In one embodiment, the method for monitoring the wound healing by detecting xanthine in the wound comprises contacting a wound care substrate with a wound or biofluid of a subject, wherein the wound care substrate comprises an enzymatic electrochemical sensor comprising an electrode functionalized with XO on the surface of the electrode with nano-materials; and measuring an electric signal or a change in the electric signal.

Figure 5:
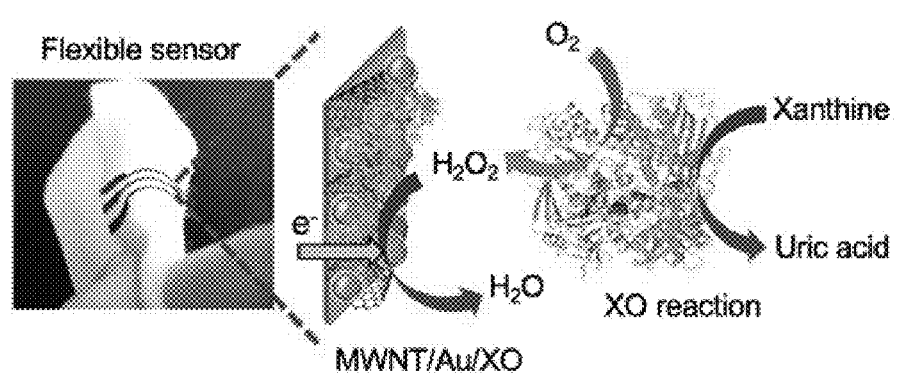
FIG. 5 shows a flexible biosensor on a wound dressing modified with MWNT and Au (left). XO reaction and electron transfer mechanism (right).

In one embodiment, a combination of MWNT and gold nanoparticles (Au) is used as the catalyst for monitoring XO enzymatic reaction. While the use of MWNT enhances the conductivity of the working electrodes providing improved response, the use of Au nanoparticles provides the biosensor with its biocompatible edge to target healthcare innovation (FIG. 5).

Figure 1C:
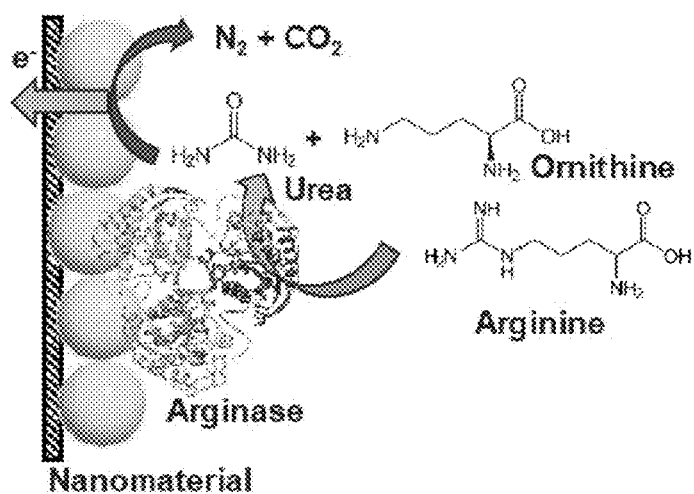

Arginine is another biomarker that is metabolized to urea and ornithine by an enzyme, arginase (FIG. 1c). This pathway is important in the healing process as it generates nitric oxide, a molecule involved in immune responses, proline, a substrate for collagen synthesis, and polyamines, that stimulate cellular proliferation. Due to metabolism, levels of arginine can critically reduce on injury. Thus, to accelerate healing and increase collagen deposition for treatment efficacy, it is advantageous to monitor arginine levels and determine personalized therapeutic needs.

In one embodiment, the method for monitoring/assessing the wound healing by detecting adenosine in the wound comprises contacting a wound care substrate with a wound or a biofluid of a subject, wherein the wound care substrate comprises an enzymatic electrochemical sensor comprising an electrode functionalized with adenosine deaminase on the surface of the electrode with nano-materials; and measuring an electric signal or a change in the electric signal.

Advantages of certain embodiments of the subject invention include, but are not limited to: 1. personalized wound care devices, 2. non-invasive precise detection of biomarkers for wound healing, 3. integration of sensor system on a flexible wound care platform (fabric/bandage/gauze/dressing material), and 4. monitoring treatment and tissue regeneration for personalized therapy.

The subject invention further provides: 1. enhanced selectivity through nano-material catalysts; 2. superior activity and loading through ionic polymer, 3. use of redox electron shuttle for improved sensitivity; 4. sensor-fusion and computational approach to (i) eliminate false readings from other wound fluid contaminants, and (ii) calibrate the sensor, for addressing stability; 5. integration of sensor system on flexible wound care platform (fabric/bandage/gauze/dressing material); and 6. monitoring treatment and tissue regeneration for personalized therapy.

The system facilitates stable and selective detection of biomarkers in rapid wound diagnostics. This technology transforms wound care with efficient and effective wound management on a wearable healing platform. One such example is tracking severity of wounds, for example, in diabetics.

In one embodiment, the enzymatic electrochemical sensing system may be used for skin protection and ulcer prevention, wherein the enzymatic electrochemical sensing system is placed on intact skin of a subject.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably. Use of the term comprising contemplates other embodiments that "consisting of" or "consisting essentially of."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

EXAMPLES

Experimental Section

Materials and Methods
Materials

Urate oxidase (UOx) lyophilized powder containing 15~30 U mg$^{-1}$ was purchased from Sigma Aldrich. XO lyophilized powder containing 15-30 U mg$^{-1}$ was purchased from Sigma Aldrich. The electron transfer mediator ferrocene carboxylic acid was purchased from Chem-Impex International, Inc. Poly (vinyl alcohol) N-methyl-4(4'-formylstyryl)-pyridinium-metho-sulfate-acetal (PVA-SbQ) purchased from Polysciences, Inc., was used to entrap the UOx on the screen-printed carbon electrode (SPCE) purchased from CH Instruments, Inc., for the construction of the UA biosensor strips. The metal precursors used for nano-material deposition were gold nanoparticles (Au), purchased from Sigma Aldrich and silver nanowires (Ag) purchased from Novarials Inc., respectively. Poly-dimethyl-siloxane sheet (1000×1000×1 mm) purchased from GoodFellow, was used as the substrate for low volume sample studies. Xanthine, UA, hydrogen peroxide, sodium phosphate monobasic ($NaH_2PO_4$), sodium phosphate dibasic ($Na_2HPO_4$), sodium hydroxide (NaOH) and boric acid were used of analytical grade. All aqueous solutions were prepared using deionized (DI) water. Phosphate buffer (20 mM) and boric acid (20 mM) were used as electrolyte solutions. Phosphate buffer solutions (pH 5 to 8) were prepared using $NaH_2PO_4$ and $Na_2HPO_4$ salts. Boric acid buffer solutions were prepared for pH 8 to pH 10 solutions. Sodium hydroxide (NaOH) solution prepared in DI water at pH 12 was used for electrochemical studies. MWNTs (o.d.=10-20 nm, i.d.=2-10 nm and length=0.5-200 μm), and 20 nm Au nanoparticles were purchased from Sigma Aldrich. Conductive graphite and Ag/AgCl pastes (Gwent Group, UK) were used for preparing the flexible electrodes on adhesive vinyl (Silhouette America, USA). 0.2 U $ml^{-1}$ horseradish peroxidase (HRP) and 50 μM Amplex red reagent of analytical grade from ThermoFisher Scientific were used for fluorescence studies. Colorimetric UA assay kit from ThermoFisher Scientific was used for human sample studies.

Apparatus and Methods

Cyclic voltammetry (CV) and differential pulse voltammetry (DPV) were performed using the analytical system model CHI-230B potentiostat from CH Instruments, Inc. The electrochemical characterizations of the enzymatic electrode were carried out in a conventional three electrode cell assembly consisting of Ag/AgCl as reference electrode and Pt wire as counter electrode. For low volume sample studies and sweat studies, the experiments were carried out on the SPCE surface containing Ag/AgCl as reference electrode and carbon coating as counter electrode. In both cases, the working electrode was the bare SPCE or modified SPCE. The SPCE used were modified with (i) PVA-SbQ (polymer), (ii) UOx (physiorbed), and (iii) UOx in PVA-SbQ (entrapped). In these experiments, 0.0532 mg $cm^{-2}$ PVA-SbQ was used to immobilize 0.25 U $cm^{-2}$ UOx on the electrodes. Prior to immobilization, the SPCEs were polished with 0.05 m alumina slurry and rinsed thoroughly with DI water.

All the immobilizations were carried out by drop casting, nitrogen drying, and respective electrolyte rinsing prior to testing. The immobilization steps involving UOx were carried out in ice box to prevent its denaturation. All potentials were reported with respect to Ag/AgCl reference electrode. The effect of pH on the enzyme activity was performed in Evolution 201 UV-Visible Spectrophotometer, ThermoFisher Scientific. SEM images of the nanostructures on the sensor surface were measured using scanning electron microscopy (SEM) 6330/JEOL FE-SEM. Material characterization studies on the electrode surface were performed using Raman spectroscopy with a 514.5 nm Ar laser, impedance measurements with Gamry impedance analyzer, SEM JEOL 6330, ThermoFisher Scientific and confocal microscope (Nikon Instruments Inc., Melville, N.Y.). A Nikon C1 confocal microscope provided images of different intensities emitted from various enzyme loading. CV was performed to assess the performance of the nanomaterial enzyme functionalized electrode in different concentrations of xanthine prepared in PBS at pH 7.8. These measurements were performed at 20 mV/s to record the generated $H_2O_2$ at the cathode between −0.1 V and −0.6 V. All potentials have been reported with respect to the Ag/AgCl reference electrode.

UOx Immobilization

In enzyme electrochemistry, the immobilization technique determines the kinetics of the electron transfer between the enzyme and the electrode surface and enzyme loading. Immobilization methods include, for example, physisorption, chemisorption, and entrapment. The enzymatic response from both physiorbed and entrapped techniques were explored. The pKa and the isoelectric point values of UOx are 4.64 and 7.5, respectively. The net charge of the enzyme at pH 7.5 is zero and negative above pH 7.5. A cationic polymer, PVA-SbQ, was used for entrapping the enzyme. PVA-SbQ solution was prepared with DI water in a ratio of 2.5:0.5 [V/V], while 0.5 U $cm^{-2}$ UOx was prepared in 1 ml PBS buffer solution (pH 7.8). This polymer provides a stable response through ionic interactions of its freestanding polymer chains with the enzyme on the carbon of the SPCE. The cationic amide group of the styrylpyridinium side chains in the PVA backbone provides electrostatic attachment to hold the enzyme on the electrode surface. Freestanding chains of the polymer interact with the π-conjugative structure of carbon in SPCE on the electrode through π-π hydrophobic interaction. The enzymatic response from a metal nano-material functionalized substrate was also explored. 20 nm Au nanoparticles and 30 nm Ag nanowires were used.

All enzyme immobilizations were carried out by drop casting, nitrogen drying, and then vigorously rinsing in buffer prior to testing. Enzyme loading studies were carried out by keeping the volume of PVA-SbQ constant and varying UOx [V/V] in the ratio of 1:2 (53.2 μg $cm^{-2}$: 0.25 U $cm^{-2}$), 1:4 (53.2 μg $cm^{-2}$: 0.5 U $cm^{-2}$) and 1:6 (53.2 μg $cm^{-2}$: 0.75 U $cm^{-2}$). Vigorous rinsing was done to remove excess unbound enzyme. Drying in nitrogen enables removal of excess water from the electrode surface, forming a gel like structure. These immobilization steps were carried out in an ice box to prevent enzyme denaturation and leaching. For physisorption studies, 0.25 U $cm^{-2}$ UOx was drop casted on the bare SPCE and dried in nitrogen in an ice box for 10 min. After washing, 92% enzyme was retained on the electrode surface in 1:2 ratio (0.23 U $mg^2$), with more leaching occurring in higher ratio of the functionalization matrix. For fluorescence studies, the electrode was immobilized with polymer and UOx at different ratios. 20 U $ml^{-1}$ HRP was then immobilized on the electrode in the polymer UOx matrix. In the presence of 1 mM UA with 50 μM amplex red, fluorescence was observed at 570 nm.

The Flexible Biosensor Preparation

The flexible sensors were prepared by screen printing the electrodes on adhesive vinyl sheet with a mesh screen. These substrates were then coated with conductive graphite and dried in nitrogen. The electrode design was thereafter prepared using Silhouette Studio software for maintaining its precise dimensions, printed out on the graphite substrate and transferred onto wound dressing material (FIG. 3).

Conductive Ag/AgCl paste was coated to create the reference electrode. The working electrode was then functionalized with MWCNT prepared in dimethylformamide by drop-casting and dried at 60° C. Thereafter, 20 nm Au NP were deposited onto the working surface of the electrode and dried at 60° C. Then the electrode was modified with 0.2 U $cm^{-2}$ XO. Enzyme immobilization was carried out by drop casting, nitrogen drying, and respective electrolyte rinsing prior to testing. Physical adsorption of XO on the electrode surface has been a simple and cost-effective enzyme immobilization process, whereby the enzyme is attached to the transducer surface through van-der-Waal's forces and electrostatic interactions. These steps involving XO were carried out in an ice box to prevent enzyme denaturation.

Human Samples

Human sweat samples tested were collected from human subjects under institutional review board (IRB) regulations. Two different biological fluids (sweat and wound sample extracts) were studied to evaluate the biosensor. Human sweat samples were collected from different subjects after a run on a treadmill at a gym for 15 minutes. The 15 min duration was chosen because most of the subjects start sweating after 10 min. Before sample collection, a questionnaire was given to the subjects to identify any health concern. Four were collected from subjects from the age group of 25 to 35. The subjects identified themselves as African American, Hispanic or Asian. Wound fluid samples were extracted from multiple discarded wound dressings of patients at a wound clinic. To extract UA from the wound dressings, they were heated at 37° C. for 45 min in NaOH solution (pH 12) and ultra-sonicated in a homogenizer for 60 s at 20 Hz. This extract was used as a sample to run electrochemical assay measurements with standard addition method calibrated against the known concentrations of analyte. For both sweat and wound extract measurements, CV was used. The three-electrode setup and the experimental conditions were same as mentioned in the previous sections. The ThermoFisher Scientific microplate absorbance reader (570 nm) was used to conduct assay experiments using standard UA assay protocols for both biological sample extracts.

Example 1—SEM Characterization of Metal Nanostructures

Platinum, silver and gold nano-material were explored for detection of byproduct, hydrogen peroxide, and UA on the nano-structure modified SPCE and were characterized using SEM (FIG. 6).

FIG. 6a represents the SEM image of Pt nano-flakes obtained from electro-deposition over a growth period of 15 min at 35° C. This growth period of the flake like structures was optimized over different time periods (15-45 min) and temperatures (35° C.-75° C.). As given in the same SEM images, the Pt nano-flakes have the morphology of thin sheets arranged vertically with numerous edge planes. At 35° C. over 15 min electro-deposition period, the Pt nanoparticles show distinct, regular growth of nano-flakes, with a thickness of platelets in the range of 25 nm to 30 nm with a length of ~252 nm, at this stage of formation (FIG. 6b). The regularity conformation of these Pt nano-flakes was controlled over different deposition growth periods. SEM characterization of the Ag nano-wire deposited SPCE (FIG. 6b) provided a mesh of geometric, wire like structures with a uniform width of ~30 nm. The surface of the Ag-nanowire modified electrode surface revealed a network of even distribution of these nanowires. This regular dimension of the nano-structures assisted in detection, enhancing sensing performance as discussed in the following sections.

Au nano-particles were also explored to assess their effect on UA detection. As seen from FIG. 6c, a globular morphology of these particles was revealed. They were uniformly distributed over the electrode surface ranging from 40 to 80 nm. These nano-dots provide a superior response to detection of UA and its by-product, $H_2O_2$, as compared to Ag or Pt. This can be accredited to the advantage of a larger surface provided by their globular conformation. This allows for higher loading of the enzyme and an improved electron transfer rate. The Au functionalized electrode retains enzyme activity over a longer time, assisting in more stable and efficient detection. Results suggest that more enzyme molecules are able to bind to the Au nano-dots, which provide optimum response towards detection.

Example 2—Entrapped Enzyme Characterization

The enzyme UOx was entrapped in PVA-SbQ, a cationic polymer for immobilization on the electrode. The amine group of the styrylpyridinium side chains in the PVA backbone offers firm electrostatic attachment to immobilize the enzyme on the electrode surface. This is due to the net charge of the enzyme being partially negative (δ-) above pH 7.5. The pKa and the isoelectric point values of UOx are 4.64 and 7.5, respectively. This binding and interaction of the amino acid chains of UOx with the polymer is depicted in FIGS. 7a and b. The polymer structure in the schematic has minimized bond energy.

The UOx entrapped in PVA cationic polymer was characterized by various spectroscopic, optical and electrochemical techniques to assess the surface morphology and characteristic behavior. The physisorbed UOx on the electrode surface was used as a control in all these studies. To obtain highest loading of UOx on the electrode surface, various ratios of polymer and UOx (1:2, 1:4 and 1:6) were studied.

Figures 8A, 8B:
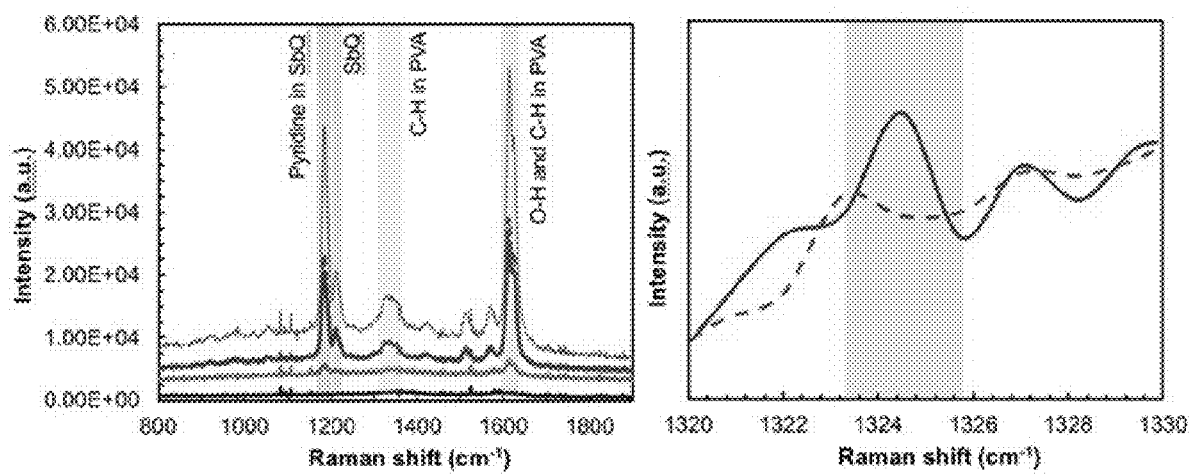
FIGS. 8A-8C show raman spectra of UOx functionalized substrates measured with 514.5 nm Ar laser. (8A) Polymer-UOx ratio 1:2 in (-) red line, 1:4 in (- - -) dashed purple line, 1:6 in (-) green line, UOx physisorbed in (-) dark blue line and pristine polymer in (-) purple line. The red, purple, green, blue bands represent the groups in PVA-SbQ. (8B) amide III (red band) and (8C) phenylalanine (green band) groups in polymer-UOx functionalized substrate.

Raman spectra of proteins consist of bands associated with its peptide chains. This technique offers several advantages for analysis of enzymes through the shifts in peak and intensity. The structural fingerprint of specific molecules in entrapped UOx-PVA-SbQ was assessed with 514.5 nm laser excitation. The spectrum exhibited in FIG. 8a depicts two main zones at intermediate (1,100-1,400 $cm^{-1}$) and high (1,500-1,700 $cm^{-1}$) frequencies. While a polymer functionalized electrode provided typical peaks at 1330.8 $cm^{-1}$ and 1613.72 $cm^{-1}$ due to —CH and —OH interactions, amine in the pyridine of PVA-SbQ showed bands at 1184.34 $cm^{-1}$ and 1214.34 $cm^{-1}$. Minute shifts in these peaks were observed for UOx functionalized electrodes, with the polymer chain interactions noticeably overshadowing the amino acid chain interactions of UOx.

Figure 8C:
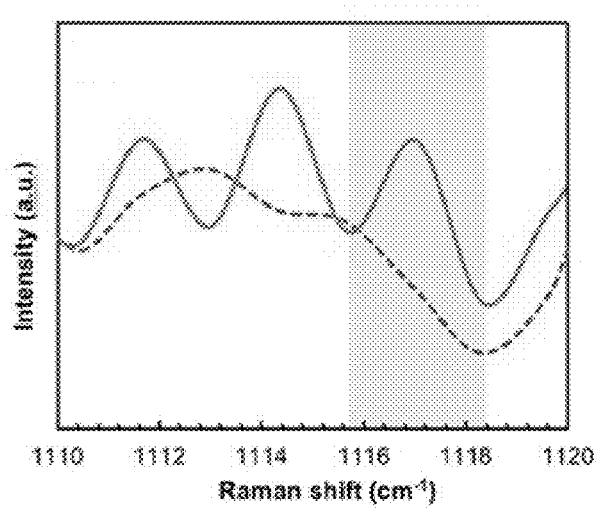
Figure 9A:
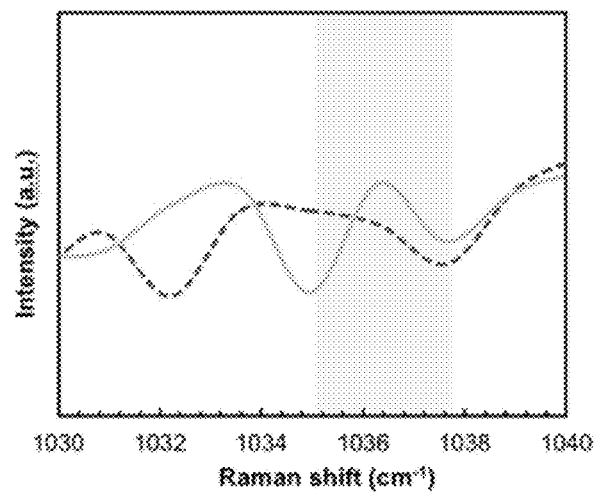
FIGS. 9A-9D show raman spectra of UOx functionalized substrate measured with 514.5 nm Ar laser, showing peaks of amino acid residues depicting bonds of (9A) C—C (yellow band) and (9B) $CO_2$— (orange band) in Arginine; (9C) C=C and —$CH_3$ in Valine (green band); and (9D) —$CO_2$— (blue band) in Leucine. The dashed purple line is the signal from pristine PVA-SbQ.
Figure 9B:
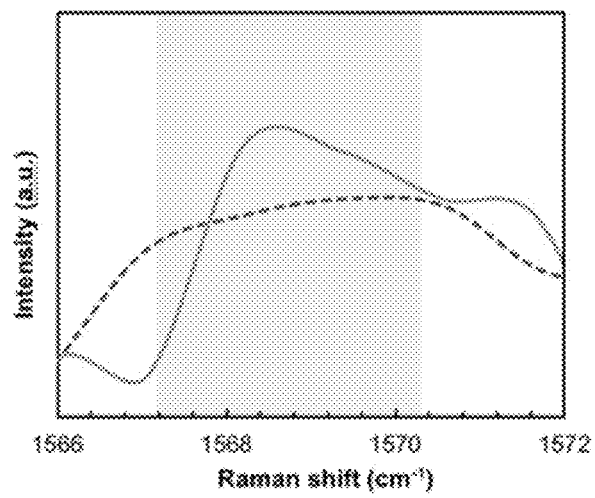
Figure 9C:
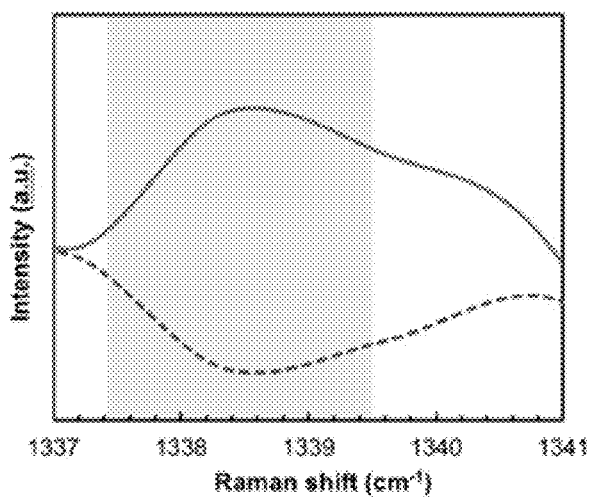
Figure 9D:
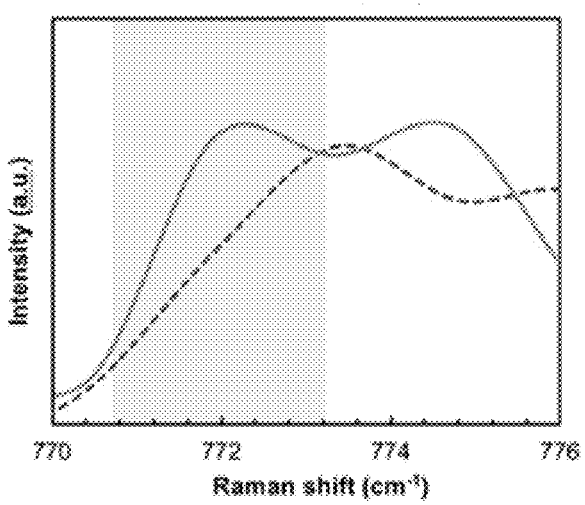

The entrapped enzymatic electrode provided distinct peaks for amide III band of UOx and phenylalanine at 1324 $cm^{-1}$ (FIG. 8b) and 1116.99 $cm^{-1}$ (FIG. 8c), respectively. This can be attributed to C—C and C—O—C bonds and changes in the a-helical structure and b-sheets of the enzyme due to electrostatic interaction between d⁻ of the amino acid chains and positive charge of pyridine in PVA-SbQ. As compared to physisorbed UOx, a slight shift of the amide I band is seen from 1578.78 $cm^{-1}$. Other amino acid residues such as leucine, valine and arginine also provided smaller intensity peaks at 772, 1037, 1339 and 1569 $cm^{-1}$ representing stretching vibrations of CH, NH and CN bonds of the carboxyl and amino groups in the UOx functionalization matrix (FIG. 9). Copper, being embedded within the amino acid chains, displayed a relatively small peak around 985.7 $cm^{-1}$. In FIG. 8a, there was a decrease in intensity of the predominant polymer peaks as the UOx volume increased (polymer:UOx ratio in electrode preparation). This decrease was due to reduced polymer concentration on the electrode surface.

Fluorescence microscopy was performed to elucidate the morphology of the UOx entrapped matrix and to visualize the UOx reaction. Along with physisorbed, the effect of three different enzyme ratios of 1:2; 1:4 and 1:6 in the hybrid PVA-SbQ/UOx system was investigated. In these studies, amplex red was used as a fluorescent tag for imaging immobilized enzyme on the electrode surface.

On enzymatic oxidation of UA, amplex red reacted with the byproduct, $H_2O_2$, in the presence of HRP to a form fluorescent product, resorufin, at 570 nm. The results (FIG. 10) offered a pictorial representation of the entrapped enzyme on the electrode surface. Increased UOx volume (polymer enzyme ratio) from 2 µL (1:2) to 6 µL (1:6) (FIGS. 10a-c) led to more un-entrapped enzyme leaching out during electrode preparation procedures forming dark empty spaces, as depicted by arrows in FIG. 10. At 1:4 and 1:6 ratios (FIGS. 10b and c), the enzymes were scarcely populated compared to the 1:2 ratio (FIG. 10a). The leaching on higher V/V ratios was due to reduced cation to anion ratio in 1:4 and 1:6 matrices as compared to 1:2, and in turn, being unable to firmly entrap the enzyme within the matrix. More distinct fluorescence is observed with sharper intensity emission from the 1:2 polymer UOx ratio (FIG. 10a). These images also denote the active sites of enzymatic UA oxidation on the electrode surface. Fluorescence intensity decreased as the ratio of enzyme and polymer increased (FIGS. 10e and 11) in the matrix. As compared to entrapped sample, physisorbed (FIG. 10d) has very low or no emission at 570 nm, indicating unstable immobilization without the polymer. These characteristics can also be observed from the SEM morphology of the 1:2 polymer UOx matrix on the working electrode (FIG. 12). The topography of the physisorbed surface has distributed enzyme with amorphous morphology on the electrode surface as seen in FIG. 12a. The enzyme entrapped in the cationic polymer (FIG. 12b) shows a more homogenous and smoother conformation, covered by the polymer coating. These imaging analyses provided visual evidence of surface functionalization for the immobilization matrix.

Electrochemical impedance studies (EIS) were carried out at 0.3 V from 1 mHz to 100 kHz in the presence of the redox shuttle, FCA, to observe its influence on the resistive and capacitive effects of different enzyme loadings in the functionalization matrices. UOx functionalized electrodes were tested using FCA redox probe (20 mM). The Nyquist plot (FIG. 13a) shows enhanced $R_{ct}$ (semicircle area) for lower polymer to enzyme ratio compared to the higher ratio (20.47 MΩ to 0.20 MΩ) with error deviation within (+/−) 5.5%. This increase in electron transfer resistance can be attributed to higher ratio of UOx in the matrix. As the thickness of the enzyme layer on the working electrode increases, fewer active sites are available on the electrode for the FCA redox reaction and, thus, electron transfer is decelerated. The semicircle portion observed at high frequencies corresponds to electron-transfer limited process, with transfer of electrons between FCA and the electrode surface. A second inflection depicted in the plot, can be accredited to the presence of multiple capacitive effects as illustrated in FIG. 13a. The straight-line portion represents diffusion-limited ion transfer process at low frequencies. $R_{ct}$ is noted to increase with increased thickness of polymer-enzyme matrix on the electrode. Negligible variation in solution resistance (Rs) was noted among them. Impedance patterns were noted to change until 2.5 MΩ at lower frequencies. At high frequencies, beyond 2500 kHz, with increased thickness of the film on the electrode, the change becomes less significant.

The Bode plot (FIG. 14) obtained from these impedance studies shows increases in phase angle with the increase in frequency. Negative phase angle denoted a lag in response, confirming formation of double layer capacitance. Electrode polarization impedance of the layer formed on the electrode is noted from the slope of the magnitude of $C_{dl}$ at lower frequencies. $C_{dl}$ formation conforms with the conjugation and binding of UOx to the electrode surface, with accumulation of charge in the double layer. With increased loading of UOx, this capacitive behavior indicates insulating properties on the surface, limiting charge transfer processes. Entrapped enzymatic electrodes have lower $R_{ct}$ values than the physisorbed due to the ionic interactions between the polymer and UOx. With increased polymer-enzyme ratio, the potential agitation also increased $C_{dl}$. Simulation and fitting of the data was performed using EIS Spectrum Analyser software. The Nyquist data obtained from EIS was fitted to an equivalent circuit (inset of FIG. 13a) to determine the charge transfer resistance ($R_{ct}$) and double layer capacitance ($C_{dl}$) at the UOx-FCA interface of the electrodes. The basic Randles circuit was modified by a secondary capacitive element, adapted by a constant phase element (CPE). Due to coulombic interactions and constant motion of FCA molecules towards and away from the electrode, constant diffusion of electrons occurs. The diffusion layer, modelled as a CPE, includes capacitive effects at 0.3 V, in parallel with $C_{dl}$ and $R_{ct}$.

Surface enzyme activity was studied for each electrode (various polymer-enzyme ratios and physisorbed) to obtain a correlation between the electrochemical behavior of the electrodes and surface activity. For electrochemical studies, the modified electrodes were tested in UA solution (48 μM) and the responses were plotted against polymer-enzyme ratios. The enzyme present on the modified electrode surface was quantified by carefully scraping and dissolving the content from the modified electrode surface in a buffer solution and running its absorbance studies at 570 nm. This enzymatic assay was used to calculate the specific activity of UOx on the electrode surface. Compared to physisorbed UOx, the 1:2 ratio polymer entrapped UOx showed 76% increased activity (FIG. 13b). However, with further increased ratio of enzyme on the surface, lower activity was noted, with more enzyme retained on the electrode surface using 1:2 ratio. Retaining capability of the enzyme reduced by 60%, ascribed to greater leaching in higher ratio of functionalization matrix. Electrochemical studies for these varied functionalized substrates were also performed. These exhibited higher current density of ~3.42 mAcm$^{-2}$ for 1:2 matrix ratio. With vigorous washing of the electrode to remove excess un-entrapped enzyme, increased ratio of enzyme on the electrode surface provided reduced current density, which is consistent with the specific activity results and other characterizations. All these entrapped UOx characterization studies established the immobilization ratio and provided evidence for the highly active enzyme presence on the electrode surface using 1:2 matrix ratio.

Example 3—Uricase—a Natural Catalyst for UA Detection

UOx is an enzyme that belongs to the catabolism of the purine degradation pathway. It plays an integral role in the enzymatic conversion of uric acid ($C_5H_4N_4O_3$) to 5-hydroxyisourate ($C_5H_4N_4O_4$) through oxidation (Eq. 1). The formed 5-hydroxyisourate reacts with water to produce carbon dioxide and allantoin ($C_4H_6N_4O_3$) (soluble form of urate) (Eq. 2). The oxidation of urate to racemic allantoin occurs through the formation of unstable intermediates. In this reaction, C-5 of urate is converted to C-4 of allantoin, while C-2 of urate was recovered as C-2 of allantoin. Yield of the byproduct ($H_2O_2$) from this reaction was utilized in well-established colorimetric assay techniques to quantify UA.

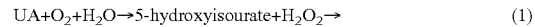

$$UA + O_2 + H_2O \rightarrow \text{5-hydroxyisourate} + H_2O_2 \rightarrow \qquad (1)$$

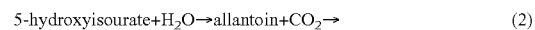

$$\text{5-hydroxyisourate} + H_2O \rightarrow \text{allantoin} + CO_2 \rightarrow \qquad (2)$$

The domain structure of UOx is 50 Å long with a 12 Å wide tunneling fold (T-fold), and is formed from the union of dimers stacked via hydrogen bonds. It is a globular homotetrameric enzyme with four identical active sites in its quarternary structure at the interfaces between its four subunits. With no metal or organic factor required for catalysis, UOx is made of 303 amino acid residues, 15 of which are involved with the active site. Among these residues, Leu170 forms a hydrophobic floor beneath the substrate and plays a role in its positioning. Three of the conserved residues (Arg176, Val227, and Gln228) within each active site act as ligand tweezers to bind and hold the substrate in place. Within the active site, Asn254 from one monomer and Thr57 from another tightly hydrogen bond a single water molecule, assisting in uric acid oxidation. Due to factor-independent reactions, direct electron transfer on the electrode surface cannot be achieved in UOx. However, the byproducts of UOx reactions can be electrochemically monitored.

The enzymatic oxidation of uric acid involves two-electron reduction of oxygen (co-substrate) to $H_2O_2$. This reaction was quantified by measuring the formed $H_2O_2$, and involves the transfer of electrons from $H_2O_2$ oxidation to FCA. In this approach, instead of monitoring $H_2O_2$ directly on the electrode surface (around $Ep_c$~-0.2 V), FCA redox shuttle was used to avoid the interference from electrochemical oxygen reduction signal (around $Ep_c$~-2.0 V). To confirm the electron transfer between $H_2O_2$ oxidation and FCA, studies were performed with different concentrations of $H_2O_2$ using UOx entrapped electrode. Results show that there was an increase in $Ip_a$ (at $Ep_a$ 0.38V) with respect to $H_2O_2$ concentration, indicating that there is an electron transfer from $H_2O_2$ oxidation to the electrode through FCA.

Example 4—Electrochemical Response of Metal Nanostructures Towards $H_2O_2$

UOx enzyme oxidizes uric acid to 5-hydroxy-isourate its byproduct, $H_2O_2$. Most of the currently available electrochemical uric acid biosensors detect uric acid through the reduction or oxidation reaction of $H_2O_2$ (generated by the UOx) on the sensor surface as shown in equation 1.

In detection of $H_2O_2$, the redox reaction at the electrode surface was studied using different nano-material. To improve the catalytic activity (Eq. 1), metal nanostructures (Pt, Ag and Au) were incorporated on enzyme functionalized electrodes. Owing to their superior electro-catalytic performance, these materials have been studied extensively for peroxide detection in enzymatic electrochemical studies. Reduced hydrogen peroxide may however interfere with that of dissolved oxygen and provide overlapping disruptions, making precise analyses difficult. In this work, the growth of these metal nanostructures has been investigated to monitor increase in electro-catalytic performance towards detecting $H_2O_2$ on the anode. The amount generated on oxidation, provides a correlation with the concentrations of uric acid in detection.

Nanostructures of Ag in the form of nano-wires were explored for their electro-catalytic performance to $H_2O_2$ detection on Ag functionalized SPCE. In the presence of $H_2O_2$, small anodic peak currents were observed at Epa around 0.35 V and 0.5 V (FIG. 15). Increase in Ipa was noticed with 0.1 M $H_2O_2$. For lower concentrations, comparatively lower response was obtained on the Ag decorated electrode.

SPCE functionalized with Pt nano-flakes were also investigated for their electro-catalysis towards $H_2O_2$ detection. In the presence of $H_2O_2$, a small anodic peak current was observed at an $Ep_a$~0.3 V due to oxidation of platinum. With the presence of 9.82 µM $H_2O_2$, a distinct increase in $Ip_c$ was observed at an $Ep_c$~-0.2 V, due to reduction of $H_2O_2$. With increased concentrations of $H_2O_2$ to 1.43 mM, $Ip_c$ was seen to increase with consistent increase in concentrations, while a decrease in $Ip_a$ was noticed. $Ip_c$ exhibited a linear response from 9.83 µM to 1.43 mM.

Electro-catalytic performance of Au nanoparticles towards the $H_2O_2$ oxidation was also assessed by cyclic voltammetry. Response of Au nanoparticles' modified SPCE was assessed in the absence and presence of $H_2O_2$ in PBS at a scan rate of 20 mV s$^{-1}$. With pM concentrations of $H_2O_2$, an increase in anodic current was observed at an $Ep_a$~0.45 V, which can be attributed to the oxidation of $H_2O_2$. As concentrations of $H_2O_2$ were increased from pM to nM, $Ip_a$ was further seen to increase. This suggested that the Au nanoparticles acted as electro catalysts in $H_2O_2$ detection. The anodic peak current increased to around 10-fold in the presence of $H_2O_2$, exhibiting a sensitivity of 0.424 µA M$^{-1}$ mm$^2$ with a linear response over a small range from 45.76 µM to 45.76 nM.

Based on the response of different metal nano-assemblies evaluated for detection to $H_2O_2$, as compared to the flakes of Pt or nano-dots of Au, the Ag nano-wires were seen to provide higher current to $H_2O_2$. Their long cylindrical forms have created a mesh-like network which provided larger area and space for the analyte to interact with the modified electrode surface.

Example 5—Electrochemical Performance of the Nano-Biosensor Towards UA Detection The use of polymer matrix of PVA-SbQ to entrap the enzyme, on metal nano-material functionalized electrodes, retains the enzyme activity over a considerable duration with minimum leaching and degradation of the enzyme. The metal nano-structures-modified electrodes provide higher current. Enzyme-substrate and electrode-substrate interactions can be improved with proper immobilization of the enzyme using this polymer.

Electrochemical studies for detection were conducted with a ferrocene based mediator, FCA, which assisted in enhanced reaction rates. This redox electron shuttle enables electron transfer between the enzyme and the nano-material modified electrode surface at a lower potential. It provides an improved response without interference from dissolved oxygen. Current response from an enzymatic electrode in the presence of FCA increases from 3 to 6 µA without interference from $O_2$ at an $Ep_a$~0.3V. Acting as an electron acceptor for the enzyme, UOx, this mediator has proven effective for enhanced electron transfer between the active site of the enzyme and the active area of the electrode.

To understand the electro-analytical performance of this biosensor, CV response was recorded with the different nano-material modified substrates in the presence of UA. The nanostructured support matrices provide several advantages over others, providing a larger surface area for enzyme immobilization, and a surface that is highly conductive and stable for enhanced performance through the π-π hydrophobic interactions of the carbon scaffolds on the electrode. CV response at 20 mV s$^{-1}$ from the Pt nano-flakes-modified SPCE was obtained for enzyme functionalized electrodes in UA. Using Pt, anodic current increases at an $Ep_a$~0.3 V. $Ip_a$ increases significantly around the same potential with FCA (FIG. 16a). Ag nano-wires provide a small increase in anodic current as seen in FIG. 16b. The enzyme-functionalized Ag nano-wire electrode provided an increase in current by ~20 µA, for analyte concentrations from 86 µM to 0.5 mM, as depicted in FIG. 16b.

An enzymatic substrate functionalized with Au nanoparticles was evaluated over a wider physiologically relevant range (14 µM to 0.5 mM) for potential non-invasive detection from sweat. The Au nano-structures-modified enzymatic biosensor provides comparatively higher current at lower concentrations with enhanced responses as depicted in FIG. 17. This nano-material modified enzymatic biosensor provides consistent increase in Ipa at an Epa of 0.3 V. With a detection limit as low as 14 µM, it can be ascertained that the designed biosensor can be utilized to detect UA levels from sweat, known to contain 25-30 µM of the analyte. This biosensor provides a sensitivity of 0.14 µA µM$^{-1}$ cm$^{-2}$. Consistent increase in response with increasing analyte concentrations is depicted in FIG. 17b. Efficient detection and enhanced response can be ascribed to the increased active surface area and conductivity provided by the uniform dispersion of the spherical Au nano-particles on the electrode surface. Results show that Au nano-material can be a catalyst for non-invasive UA detection over the physiological range.

Example 6—UOx Reaction Mechanism

To monitor the reaction on the electrode surface, either direct electron transfer (DET) or mediated electron transfer (MET) can be applied. For example, in widely used oxidase enzymes, FCA receives electrons from the enzyme's cofactor leading to MET. Glucose oxidase with flavin adenine dinucleotide (FAD) is one such example, where FCA acts as an electron shuttle between FAD and the electrode. Electron transfer from FAD (E°=−0.22 V) to FCA (E°=−0.4V) is more favorable than $O_2$ (E°=0.81 V). FCA was used as an electron transfer mediator to quantify the UA oxidation on UOx electrode, as shown in Eq. 3 and 4. The reduced $Fe^{2+}$ (metal ion in FCA) undergoes a facile one-electron oxidation on the electrode to the ferricinium state.

$$\text{Uric Acid} + Fe^{3+} \rightarrow \text{5-hydroxyisourate} + Fe^{2+} \rightarrow \quad (3)$$

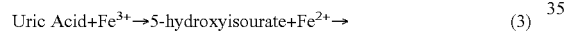

$$Fe^{2+} \rightarrow Fe^{3+} + e^- \rightarrow \quad (4)$$

However, UOx does not have any prosthetic group or cofactor. The E° of UA (E°=0.59 V) being 0.99 V is higher than FCA. The electron transfer from the active site of the UA reaction to FCA is thermodynamically not feasible (Eq. 3). Instead, the electron transfer is more favorable to the native two electron O2 reduction reaction forming $H_2O_2$ (Eq. 1). To understand the interactions between the enzymatic oxidation of UA and FCA, four different experiments were conducted as given in FIG. 18: (i) behavior of FCA redox couple, (ii) inhibition of $O_2$ in the enzymatic reaction, (iii) inhibition of $H_2O_2$, and (iv) $H_2O_2$ assay studies, to monitor FCA interaction.

Behavior of FCA Redox Couple:

The predominance of $Fe^{2+}$ ions in the natural state of FCA can be seen in FIG. 18a in the first cycle, where the Ipa ($Fe^{2+} \rightarrow Fe^{3+}$) is 0.6 times higher than the second cycle ($Fe^{3+} \rightarrow Fe^{2+}$) (Eq. 5). However, as seen in the subsequent cycle, the redox ions attained equilibrium (Ipa=Ipc). Hence, both ions are prevalent at the electrode surface.

$$Fe^{2+} - e^- \rightleftharpoons Fe^{3+} + e^- \rightarrow \quad (5)$$

Figure 18B:
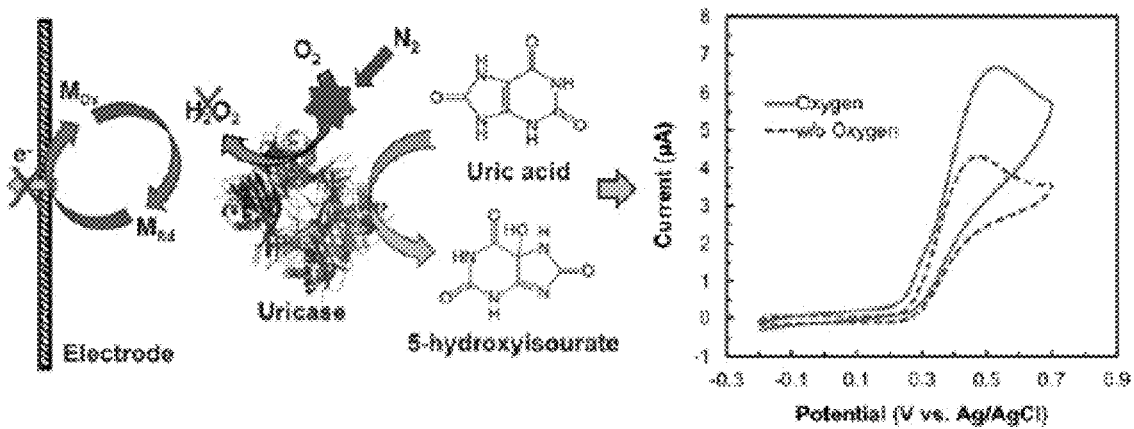

Inhibition of $O_2$ in the Enzymatic Reaction:

To understand the role of $O_2$ in electron transfer, the electrode system has been investigated by testing in the resence and absence of saturated $O_2$. Results show a significant decrease in Ip$_a$ in the absence of $O_2$ (FIG. 18b). This decrease can be attributed to nil or limited production of $H_2O_2$. In the absence of $H_2O_2$, no electron has been transferred from the active site of the enzyme to the electrode through FCA. This also shows that FCA cannot receive electrons directly from enzymatic UA oxidation (active site). In the absence of $O_2$, some response has been observed due to difficulties in eliminating $O_2$ completely from the saturated solution.

Figure 18C:
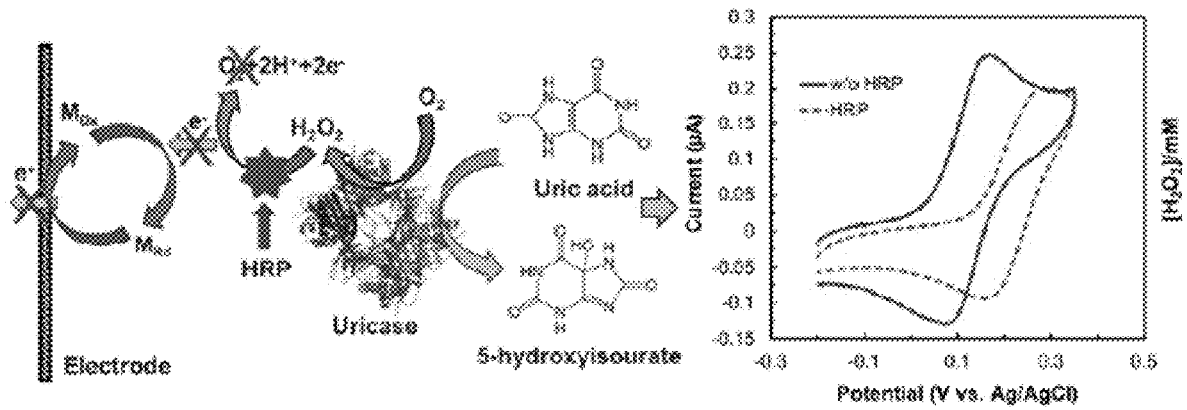
Figure 19:
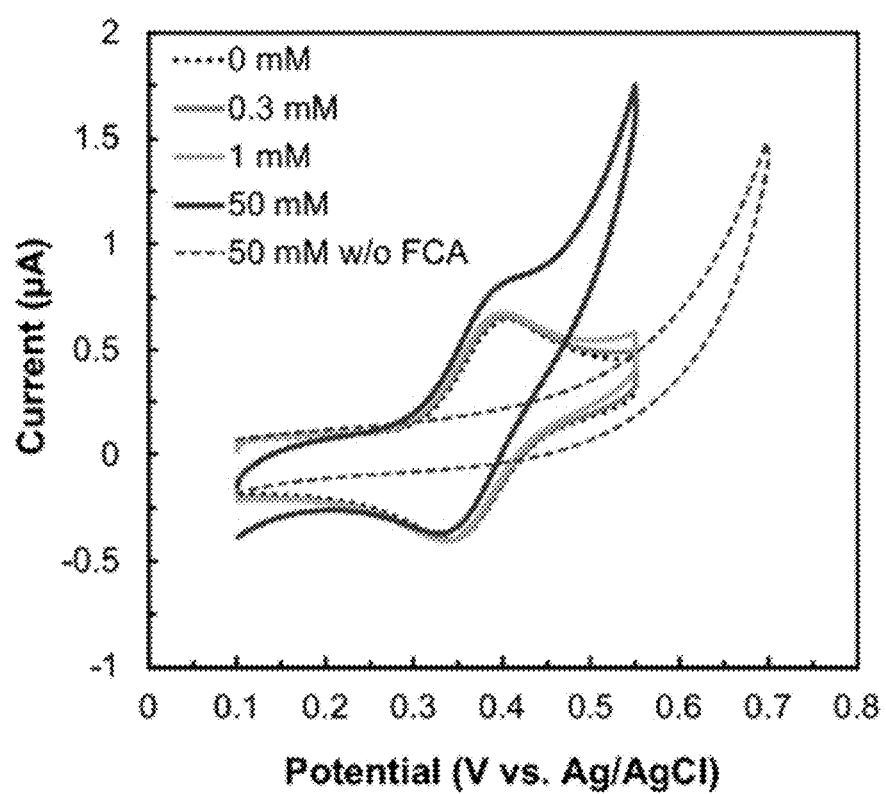
FIG. 19 shows CV response of UOx entrapped electrode in the presence and absence of 20 mM FCA to 0, 0.3, 1, and 50 mM $H_2O_2$ at a scan rate of 20 mV $s^{-1}$. This reveals that FCA acts as an electrochemical mediator for $H_2O_2$ oxidation.

Inhibition of $H_2O_2$:

The importance of $H_2O_2$ in the electron transfer mechanism has been investigated by consuming the generated $H_2O_2$ with the use of HRP and blocking its reaction with FCA. Results from FIG. 18c show a decrease in Ip$_a$ in the presence of HRP as compared to its absence. This also shows that electron transfer occurs through its by-product $H_2O_2$ to FCA and the electrode surface. The interaction between the formed $H_2O_2$ and FCA is seen in FIG. 19, where there is a decrease in Ep$_a$ by 150 mV and an increase in Ip$_a$ by 60% (at Ep$_a$ 0.38 V) in the presence of both FCA as well as $H_2O_2$. This indicates that $H_2O_2$ (E°=0.68 V) acts as a reducing agent in the reaction, with plausible electron transfer to FCA (E°=−0.4 V). On the same electrode (FIG. 19), in the absence of FCA, there was no defined electrochemical peak, showing no $H_2O_2$ oxidation in the same potential window.

Figure 18D:
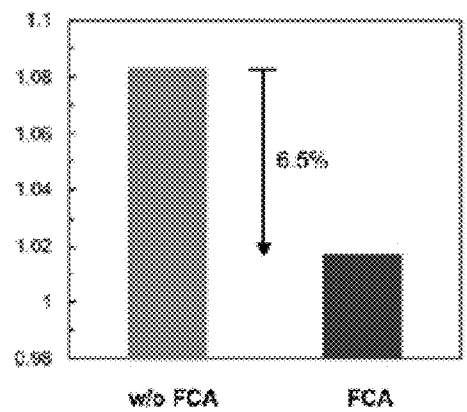

$H_2O_2$ Assay Studies:

Sampling of electrolyte solutions from the above reactions was performed to show that $H_2O_2$ was consumed during FCA redox reaction (FIG. 18d). These results show that in the presence of FCA, there is a 6.5% decrease in $H_2O_2$ concentration, while in the absence of FCA, the $H_2O_2$ concentration remained unchanged.

All the above results support that electron transfer from $H_2O_2$ to FCA (Eq. 6) is thermodynamically more favorable than the UA reaction at the active site to FCA (Eq. 3).

$$Fe^{3+} + H_2O_2 \rightarrow Fe^{2+} + O2 + 2H+ + 2e- \rightarrow \quad (6)$$

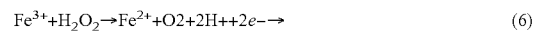

Example 7—Electrochemical Response of the Enzymatic Biosensor

Determination of UA was performed through the monitoring of $H_2O_2$ oxidation. The electron transfer mechanism that involves the oxidation of $H_2O_2$ to oxygen and the reduction of FCA is shown in Eq. 4 and 6. The reduced $Fe^{2+}$ (metal ion in FCA) undergoes a facile one-electron oxidation on the electrode to the ferricinium state. This electron transfer gives a measure of the oxidized $H_2O_2$, which in turn can be used to quantify UA oxidation.

FCA can be used as a redox electron shuttle in enzyme studies. Ferrocene, through reversible oxidation, generates ferrocinium ions (Fe$^+$) under low potentials. Its characteristics make it useful in facilitating the monitoring of enzyme activity at the electrode surface by meeting the conditions of (i) reversibility, (ii) no pH dependency, and (iii) generation of stable redox forms that do not react with oxygen. The signal of the oxidized $H_2O_2$ in the presence of FCA can be seen in FIG. 20a. For FCA at a pH of 7.8, a bare electrode has an Ep$_a$ of 0.4 and an Ip$_a$ of 2.6 µA. On the same electrode, the peak separation, ∆E (30 mV) and peak currents (Ip) of the anode and cathode show that FCA undergoes a reversible redox reaction.

The formal potential (E°) of all three electrodes (bare, enzyme entrapped and physisorbed) for FCA is 0.385 V, while Ep$_a$ and ∆E remains the same for all three. In the presence of 48 M uric acid, there was an 800 nA increase in Ip$_a$ on the bare electrode. With the addition of polymer on the electrode, however, Ip$_a$ decreased by 350 nA. The working area of the electrode was blocked, thus preventing sufficient diffusion of the analyte to its working area. In comparison, a UOx physisorbed electrode provided a better response to $H_2O_2$ with a 400 nA increase in $Ip_a$, compared to the bare electrode due to the hydrophilic nature of the enzyme. Additionally, the UOx entrapped electrode showed a superior response with an 800 nA increase in $Ip_a$ compared to the bare electrode. This increase can be attributed to an improved diffusion of the analytes to the electrode's working area through the polymer enzyme hybrid matrix. The double fold increase in the $Ip_a$ of entrapped compared to physisorbed shows that there was an increase in enzyme loading in the electrostatic polymer matrix. Compared to the other two electrodes, the enzyme entrapped electrode has a characteristic stead state response in the scan beyond 0.4 V.

Figure 20A:
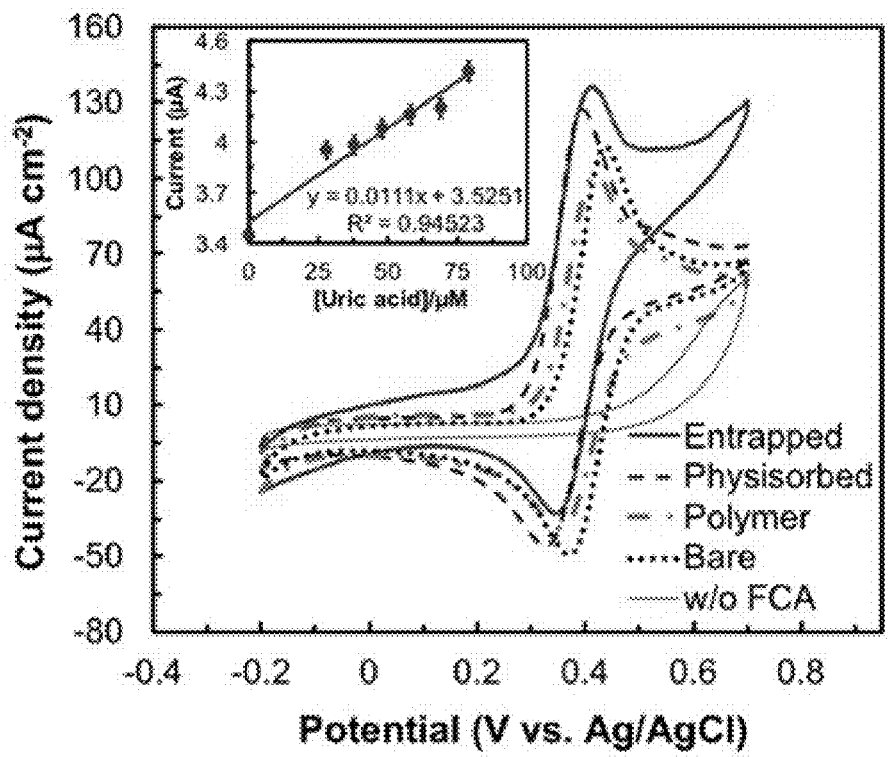
FIGS. 20A-20B show (20A) CV response of 48 μM uric acid on bare, only polymer, UOx physisorbed and entrapped electrodes in the presence and absence of 20 mM FCA at the scan rate of 20 mV $s^{-1}$. The inset is the plot of Ipa vs. UA concentration in physiological range (12-100 μM); (20B) DPV response of 48 μM UA on UOx physisorbed and entrapped electrodes at the amplitude 50 mV in the presence of 20 mM FCA. In the inset, the continuous line represents entrapped electrode and the dotted line represents physisorbed.

The formal potential, $Ep_a$ and $\Delta E$ of the other two electrodes (entrapped and physisorbed) were seen to remain unchanged. In the presence of UA, there was increased current density by 35 $\mu A$ $cm^{-2}$ on the enzyme entrapped electrode as compared to the other three. The entrapped active surface coverage for the electrode ($\Gamma$) was obtained as $5.57 \times 10^{-14}$ $mol^{-1}$ $cm^2$ from the below equation, Eq. 7.

$$\Gamma = Q/nFA \qquad (7)$$

where; F is the faradaic constant, Q is the quantity of charge consumed with an electron transfer of n over a physical area, A. Compared to the other two electrodes, the enzyme entrapped electrode has a characteristic steady state response in the scan beyond 0.4 V. This increase can be attributed to improved diffusion of the analyte to the electrode's working area through the polymer-enzyme hybrid matrix. The double fold increase in current density of the entrapped electrode compared to physisorbed shows that there was an increase in enzyme ratio in the electrostatic polymer matrix. FIG. 20a shows that the response in the absence of FCA provided much lower signal as compared to, in the presence of FCA. This shows that FCA acts as a mediator in the reaction, enabling detection at an $Ep_a$ lower by 200 mV.

Figure 20B:
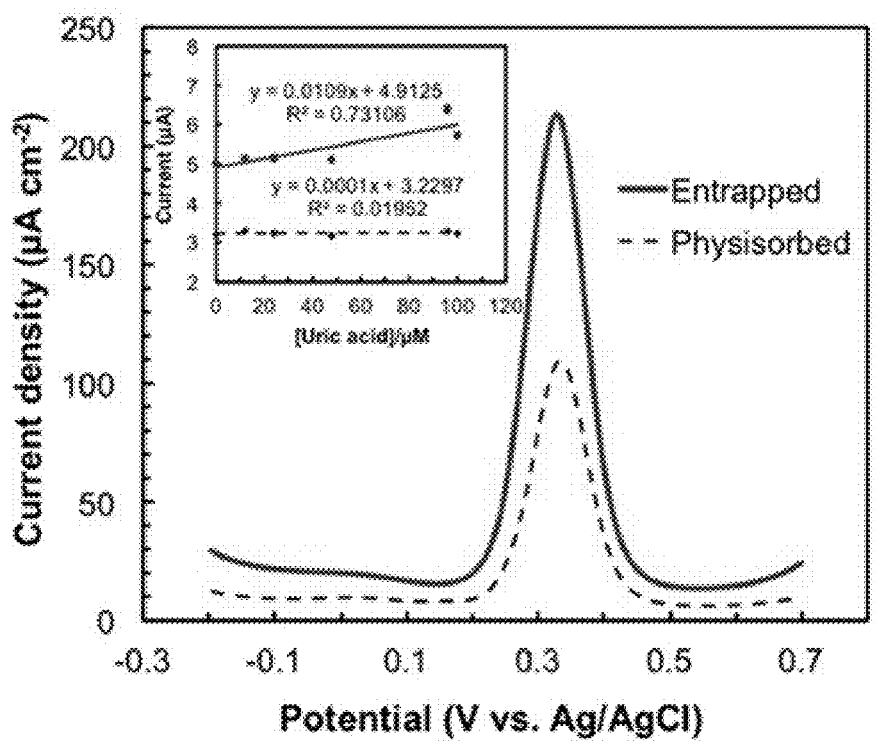

This also shows the signal is not directly from UA oxidation on the SPCE. Similarly, in the absence of UOx, the biosensor showed reduced response by 26.811%. A bare electrode in the presence of the same concentration of UA showed lower signal by 18.11%. The biosensor was evaluated by testing it with consecutive UA concentrations (0, 12-100 $\mu M$) in the physiologically relevant ranges of sweat and wound fluid. In the presence of FCA, results of the entrapped biosensor showed a linear increase in $Ip_a$ having ordinate at 3.44 $\mu A$, with a linear regression of y=0.0111x+3.5251; $R^2$=0.94523 and a standard deviation of 0.04 $\mu A$ with respect to the physiological UA concentrations (FIG. 20a inset). These studies were repeated using the DPV technique as well (FIG. 20b). Like CV, the $Ep_a$ in DPV is 0.33 V. The obtained current density in DPV was 52.3% higher than in CV, due to its ability to discriminate against charging (capacitance) currents through pulses, and its sensitivity in yielding peaks to faradaic currents.

The biosensor was evaluated by testing it with consecutive uric acid concentrations (0, 12~300 $\mu M$), where the range in the sweat for normal and chronic wounds were 20-30 $\mu M$. The results show a linear increase in the $Ip_a$ with respect to uric acid concentration (FIG. 20a inset). These studies were repeated using the DPV technique as well (FIG. 20b). Like CV, the $Ep_a$ in DPV is 0.33 V. However, the $Ip_a$ in DPV was 52.3% higher than in CV, due to its ability to discriminate against charging (capacitance) currents through pulses, and its sensitivity in yielding peaks to faradaic currents. In DPV studies, a UOx entrapped electrode provided an increase in current compared to a UOx physisorbed electrode. The linear calibration (FIG. 20b inset) also shows that the UOx physisorbed electrode cannot be used for uric acid detection due to its ultra-low sensitivity value (0.001 $\mu A$ $\mu M^{-1}$ $cm^{-2}$). Sensitivity of the entrapped electrode was 0.155 $\mu A$ $\mu M^{-1}$ $cm^{-2}$ with an ordinate of 5.01 $\mu A$ from a linear regression of y=0.01090x+4.9125, $R^2$=0.73106 and standard deviation of 79.43 nA. The physisorbed enzyme had a correlation of 0.01952 with a non-linear response with a standard deviation of 32.92 nA on the same scale as of entrapped enzyme. The UOx entrapped electrode showed superior response, with enzyme activity retained through irreversible immobilization of the enzyme on its working area.

The entrapment technique also provided improved mechanical stability and minimized leaching within its microenvironment, allowing the analyte to diffuse towards the working area of the transducer surface. Taking these factors into consideration, all analyses that followed were performed with enzyme functionalized electrodes, entrapped in a polymeric matrix using DPV.

Immobilizing an enzyme directly affects catalytic activity. The enzymatic reactions involving a single or multi-substrate with only one varying substrate follow Michaelis-Menten kinetics in Eq. 8, derived from the Lineweaver-Burk equation. The effective Michaelis-Menten constant for immobilized UOx was determined by electrochemically measuring the diffusion limited current resulting from the FCA oxidation ($\Delta Ip_a$). $\Delta Ip_a$ represents the difference between the $Ip_a$ in the presence and absence of uric acid.

$$\frac{1}{I_{ss}} = \frac{K_m}{I_{max}} \times \frac{1}{C} + \frac{1}{I_{max}} \qquad (8)$$

where, $K_m$ is the Michaelis-Menten constant, $I_{ss}$ is the steady state current measured at diffusion controlled region, $I_{max}$ is the maximum current obtained, and c is the concentration of the substrate ($4.8 \times 10^{-8}$ $mol$ $cm^{-3}$). If the rate of the enzymatic reaction is diffusion controlled, a linear relationship still exists in the above equation, but no longer has true significance with respect to Michaelis-Menten kinetics due to the diffusion limited process. Assuming the same loading of UOx on both composite as well as graphene electrodes, the $K_m$ calculated was $1.13 \times 10^{-8}$ M.

Results show that the use of FCA enabled electron transfer between the byproduct of the enzymatic reaction and the working area of the electrode. The sensitivity of the UOx modified electrode was 0.155 $\mu A$ $\mu M^{-1}$ $cm^{-2}$, with a linear concentration range of 12 to 300 $\mu M$, which includes the range of uric acid found in sweat.

Example 8—the Effect of Wound Environment on UOx

Wound healing is characterized by the successful completion of the aforementioned phases. The enzyme UOx is known to be active in alkaline environments between pH 8 and 9, with lowered activity as it deviates beyond. A key factor that influences the process is the pH of the area surrounding the wound. Chronic non-healing wounds are known to have an elevated alkaline pH (7.15 to 8.9). As healing progresses, the pH becomes more acidic, approaching that of normal skin. The pH of different biofluids namely blood, serum, urine, saliva and sweat are slightly acidic-neutral (5-7). The pH of a wound can directly impact many factors, including oxygen release, angiogenesis, protease activity, and bacterial toxicity. As enzymes can only function in specific pH environment; it is necessary to evaluate the activity of UOx in various pH environments. Doing so provides an understanding of how the wound's severity and environment affect the biosensor. This can also provide an understanding of how a wound's severity changes over time.

Figure 21:
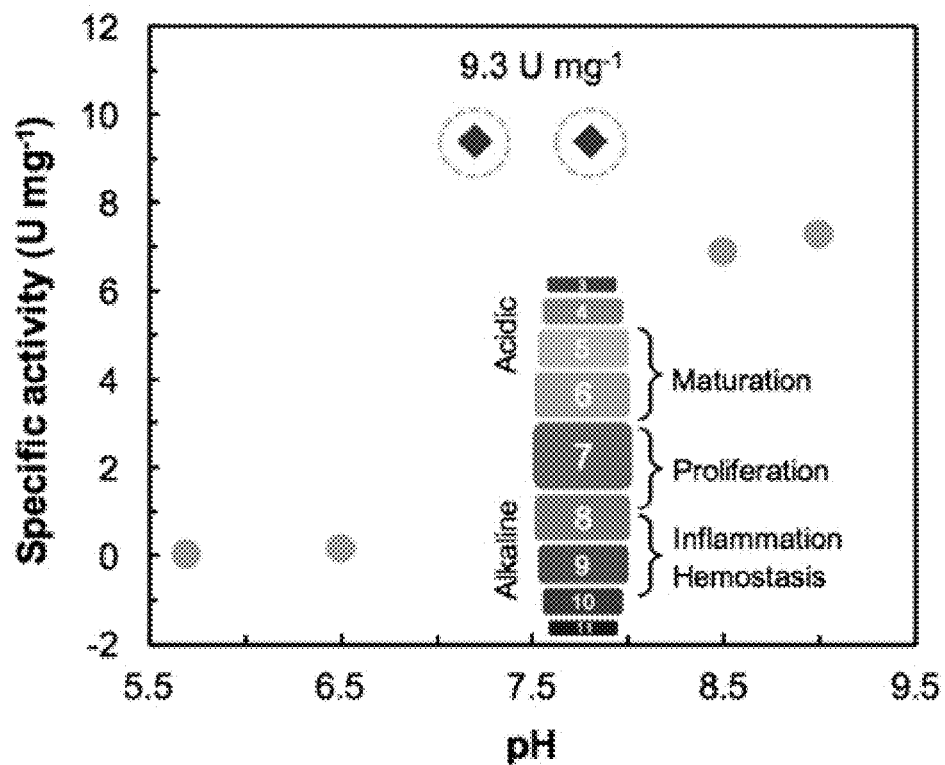
FIG. 21 shows effects of pH on the specific activity of UOx. The red diamond markers denote highest activity of UOx. The inset image represents the relationship between the wound healing stages and pH.

The diffusion of wound fluid from the epidermal layer of skin can cause it to mix with sweat in its proximity, altering its pH. It has also been seen that as a wound heals, pH shifts from alkaline to acidic. To evaluate the effect of pH, UOx was studied from pH 5 to 10 using absorption spectroscopy. The specific activity of the UOx was calculated from the absorption values and plotted in FIG. 21. The results show that the highest activity (9.3 U $mg^{-1}$) of UOx is in the pH region of 7 to 9. Based on these results, pH 7.8 was chosen for the experiments.

Figure 22:
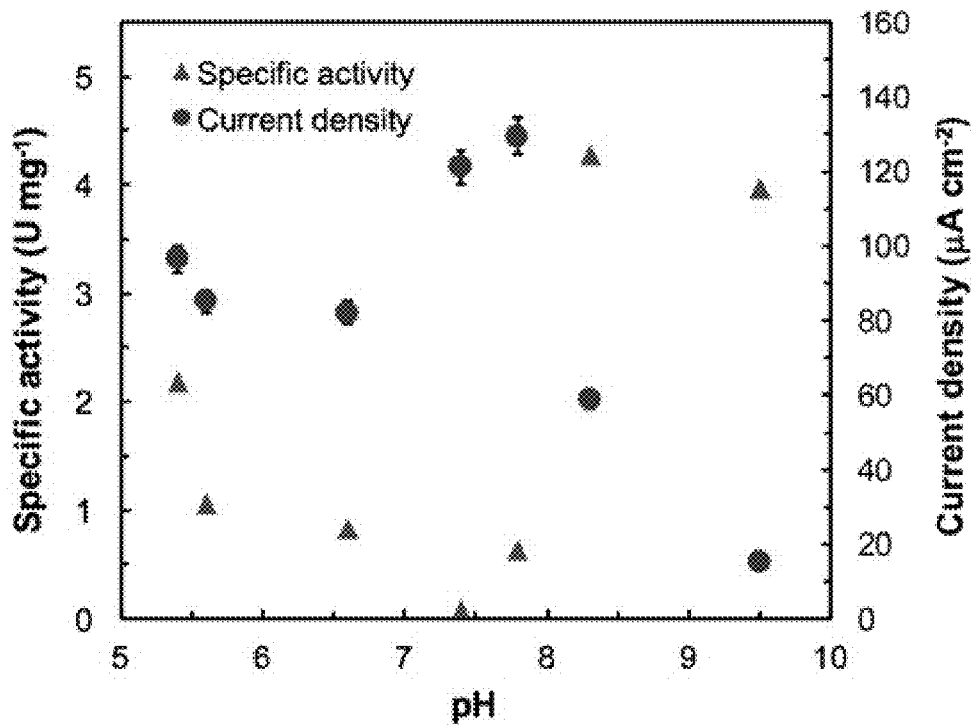
FIG. 22 shows a comparison of pH effect on specific activity of UOx and current density of UOx electrode.

Electrochemical analyses were performed over different pH to assess the change in response of UOx electrode. As depicted in FIG. 22, higher current density of ~120-130 mA $cm^{-2}$ was observed between pH 7 and 9, beyond which lower response was noted. These investigations provide an improved understanding of the pH environments suited for non-invasive enzymatic UA detection.

Example 9—Repeatability, Reproducibility and Shelf Life

It is well known that denaturation of proteins occurs at elevated temperatures and that enzymatic electrodes are unstable in nature, being sensitive to temperature and pH. Studies to determine the repeatable use of the biosensor were performed by multiple analyses of the same electrode in the same concentration of the analyte (48M) (FIG. 23a). Results show that there is a gradual reduction in response of the biosensor after using it six consecutive times. After 10 repeated analyses, the prepared biosensor showed that there was only a 20% decrease in response. Hence, the same biosensor can be used multiple times for monitoring changes in uric acid. Reproducibility studies were also performed using multiple electrodes. The behavior of these electrodes in the same concentration of uric acid were plotted to obtain a normal distribution curve (inset: FIG. 23a).

As seen from the figures, reproducible results were obtained for a frequency of 5, providing consistent current of ~6 µA. The distribution data provided a standard deviation of σ=0.5 µA for n=9, obtained from Eq. 9.

$$\sigma = \sqrt{X} \rightarrow \qquad (9)$$

where, X is the variance of the current response obtained from the different electrodes. It can be inferred that the obtained standard deviation value provides reasonable response for detection.

Studies to determine stability during continuous monitoring of UA were performed over 30 min maintaining the same concentration of UA (48 µM) (FIG. 23a) Results show that there is a gradual reduction in response after 12 min. After 20 min., the prepared biosensor still maintains 80% of the signal. With each continuous measurement up to 12 min, this biosensor can provide stable response within 10% variation over 3 days (FIG. 23c). Stability studies performed over a week in buffer solution containing UA (48 µM) showed that the entrapped sensor offered stabile signal over multiple days with repeated use. The biosensor was tested under physiological temperatures to analyze its performance and feasibility on a wearable platform. Measurements conducted at body temperature provided stable performance over a week (FIG. 23c) in the buffer solution with UA. This shows the entrapped UOx biosensor provides stable measurements of UA in physiologically relevant conditions.

The shelf lives of enzyme entrapped electrodes were studied in the same concentration of uric acid over a one week period. In this experiment, the measurements were taken once every 24 hours and the electrodes were stored at −4° C. when not in use. Results (FIG. 23) show that the electrodes had a shelf life of more than 2 days, after which there was a ~20% decrease in current. The biosensor displayed stable response for ~2 days with repeated use; and can thus be used multiple times when stored under said conditions.

Under physiological conditions, interference from electroactive species like ascorbic acid and dopamine were investigated. Healthy human sweat is known to contain ~10 µM (0.18 mg. per 100 cc.) ascorbic acid (AA). Present in abundance and in much higher concentration in extracellular fluid (46-97 µM), it is a key interferent in UA detection. Known for its biological role as an antioxidant, AA promotes healing through its role in collagen synthesis. Dopamine (DOP), an important neurotransmitter which plays a role in cutaneous wound and dermal tissue healing, is also known to be an electroactive interferent in UA detection, since its oxidation potential is very close to that of UA. Amperometric studies show (FIG. 24a) the biosensor has the response from UA within 5 s. It is observed that in the presence of AA, the baseline remains stable and unchanged over 5 s. However, in the presence of DOP, there is a shift in the baseline by 0.2 mA, after which the signal is noted to stabilize at 10 s. It can also be seen that despite interference in the presence of AA and DOP at higher physiological concentrations (100 µM), the maximum decrease in current was only 82 nA and 57 nA (20 s) in the presence of DOP (FIG. 24b). This shows that this biosensor can make reasonable measurements within the physiological range.

Example 10—Measurement of UA in Biological Samples

To evaluate this biosensor for human subject analyses, UA in samples of fluid from sweat and wound milieu was detected. When an injury occurs, fluid oozes in and around a wound through diffusion in the sweat glands and surrounding tissue in the dermal layer of skin with changes in the osmotic gradients. At the site of an injury, its vicinity also has a rise in UA concentrations. With a concentration of 20-30 µM, measuring UA non-invasively from sweat in wound proximity is relatively easy and possible.

The biosensor has been assessed by measuring UA levels present in human sweat obtained from de-identified samples collected for the study as discussed (Table 1—SS1 to SS4). These samples were measured by standard addition method in both UA assay and biosensor. A correlation between the assay and sensor measurements is drawn in Table 1. It can be seen from Table 1, that the UOx biosensor provided a varying recovery between 86.52% and 118.11% and an average RSD of 1.38%.

Figure 25C:
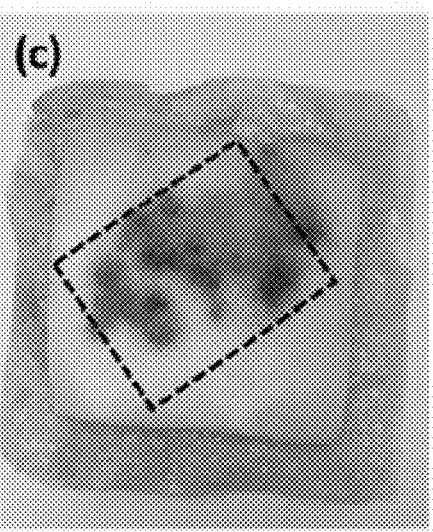
Figure 25D:
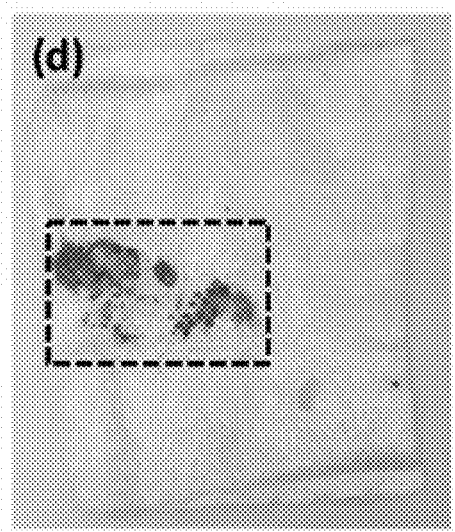

The biosensor was evaluated for UA detection in extracted wound fluid from dressing. Here, wound fluid, extraction was done from four different dressings (FIG. 25) and analyzed to determine UA concentrations using standard assay protocols. The concentration values of the samples are given in Table 1—WS1 to WS4.

TABLE 1

Colorimetric UA assay vs. electrochemical detection of human sample extracts using UOx enzymatic biosensor.

| Sample No. | Assay (µM) | Biosensor (µM) | Recovery (%) | RSD (%) |
|---|---|---|---|---|
| SS1 | 9.15 | 9.75 | 106.46 | 1.58 |
| SS2 | 29.46 | 34.79 | 118.11 | 2.19 |
| SS3 | 53.02 | 45.88 | 86.52 | 1.31 |
| SS4 | 64.29 | 63.95 | 99.45 | 0.44 |
| WS1 | 76.64 | 65.21 | 85.08 | 4.64 |
| WS2 | 96.40 | 85.11 | 88.29 | 0.45 |
| WS3 | 106.40 | 115.83 | 108.86 | 3.91 |
| WS4 | 34.02 | 50.61 | 148.75 | 10.37 |

SS and WS represent different sweat and wound sample extracts respectively.

Figure 26:
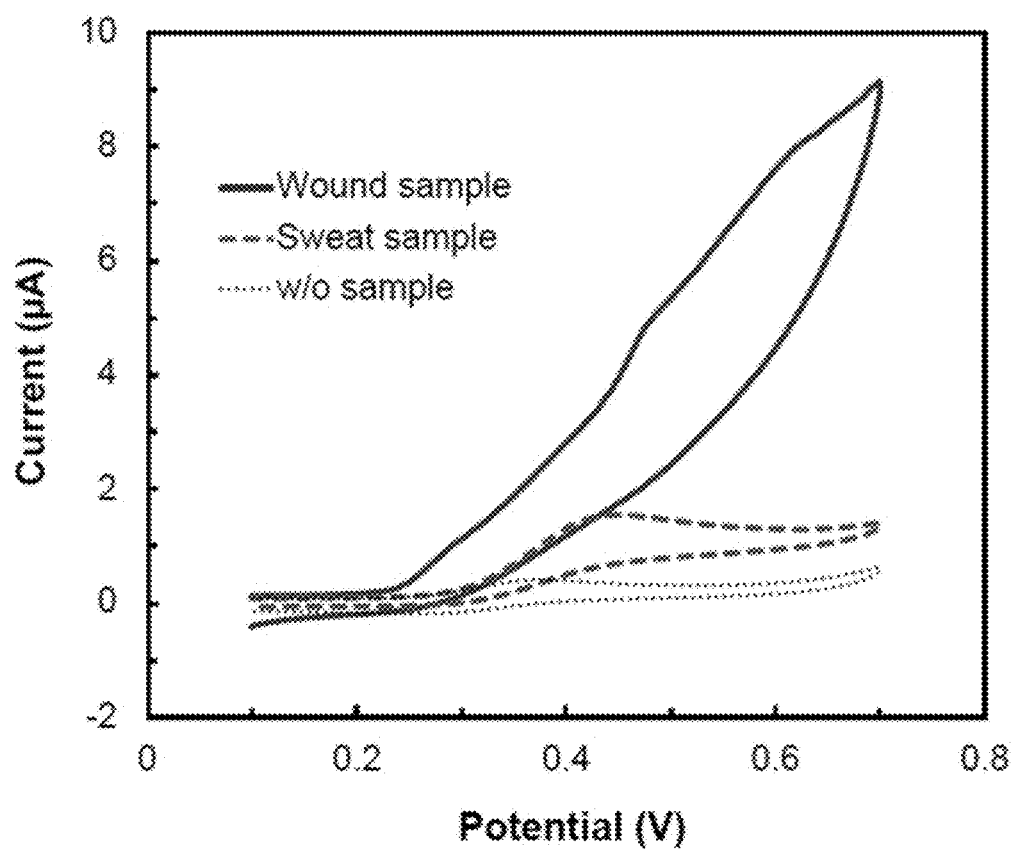
FIG. 26 shows a sample plot depicting CV response of the UOx electrode to one of the sweat and wound samples, measured at 20 mV $s^{-1}$. The data show that the wound has higher concentration of UA than sweat.

Table 1 depicts studies from four patients that provided an average recovery of 107.75% and RSD of about 5%. Patient, wound and treatment variations may lead to varying levels of electrolytes and proteins. Some deviation in response can thus be ascribed to these differences in wound fluid or sweat composition. For both sweat and wound extracts, each sample was assessed thrice. The mean of these values has been provided in Table 1. The intrinsic characteristics of the CV response obtained from a sweat and a wound sample extract have been shown in comparison with buffer (absence of sample) in FIG. 26.

This sensor has been optimized for lower detection limit with stable response for seven days at physiologically relevant temperature (40° C.), and with a controlled linear range for detection from sweat and wound extracts. This may potentially facilitate non-invasive UA detection from sweat around the wound preventing occlusion effects from embedding the sensor directly on the wound.

Example 11—Sweat Lipid Emulsification Effect on the Sensor Signal

Healing progress can also be tracked by monitoring systemic uric acid from the sweat in the vicinity of the wound. This approach is non-invasive and does not occlude the biosensor with other contaminants present in concentrated wound fluid. Measuring uric acid through sweat will be influenced by the sweat contents. Sweat, secreted from the eccrine glands of the skin, helps regulate body temperature. It is mainly composed of water with dissolved minerals, proteins, and ions. At any given time, sweat secreted by different people may have varying levels of these components.

This kind of difference in content could trigger changes in the biosensor measurements. The biosensor was tested to detect uric acid in sweat using the standard addition method. The samples were prepared by spiking known concentrations of uric acid and testing them against its linear calibration curve. As given in Table 2, two different sources were selected for this study, one clearer than the other. Increased turbidity could result from emulsification of lipid/fat molecules in certain cases. Such variations affect the electrochemical signal. The results show that Source A (Table 2) provided a positive value and Source B provided a negative one. This negative value can be attributed to the fat molecules blocking the electrode surface.

TABLE 2

Electrochemical detection of uric acid in human sweat samples using enzymatic biosensor.

| Source | Sample | Added (µM) | Found (µM) | Recovery (%) | RSD (%) |
|---|---|---|---|---|---|
| A | S1 | 30.3 | 68.8 | 227 | 4.7 |
|   | S2 | 33.9 | 69.4 | 205 |   |
|   | S3 | 37.5 | 77.7 | 207 |   |
| B | S1 | 30.3 | −32 | −106 | 97.1 |
|   | S2 | 33.9 | 7.6 | 23 |   |
|   | S3 | 37.5 | −38.4 | −102 |   |

A and B represent the sweat samples without and with fat emulsification, respectively.

Figure 27:
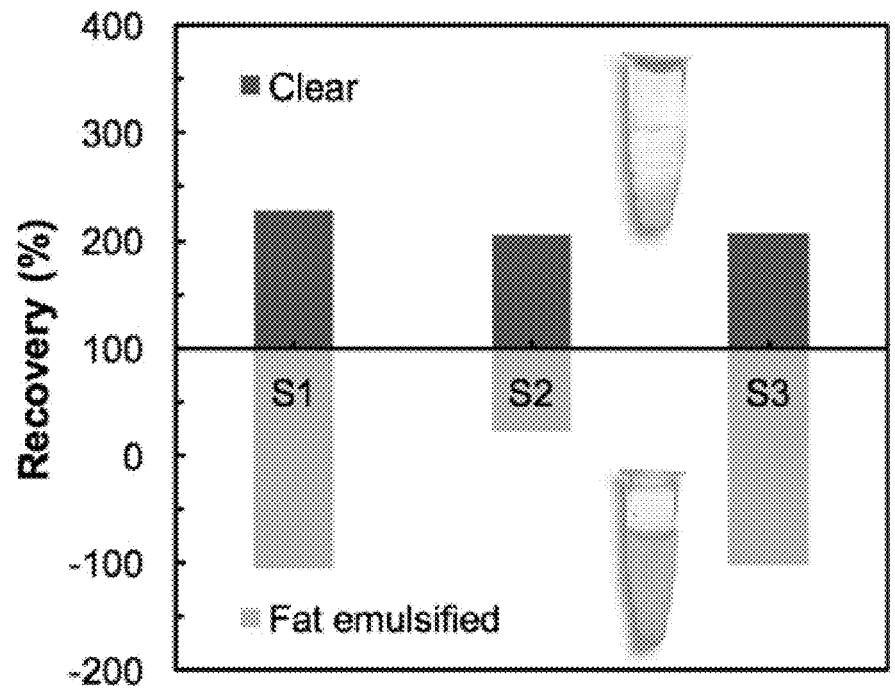
FIG. 27 shows a plot representing the effect of fat emulsification in sweat on the biosensor recovery data obtained through DPV technique. S1, S2 and S3 represent 30.3, 33.9 and 37.5 μM UA respectively. The top and bottom vial images are the clear and fat emulsified sweat samples.

The emulsification of lipid molecules could be considered a cause of a change in recovery. These results are also plotted as seen in FIG. 27 with recovery of uric acid from the sweat samples.

Example 12—Surface Morphology of Nanocomposite Electrode

Figure 28A:
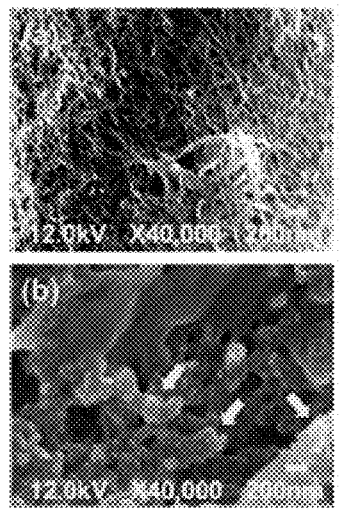
FIGS. 28A-28C show SEM images of (28A) MWCNT; (28B) MWCNT/Au; (28C) comparison of CV signals of various XO electrodes in the presence of 7.3 mM xanthine.
Figure 28B:
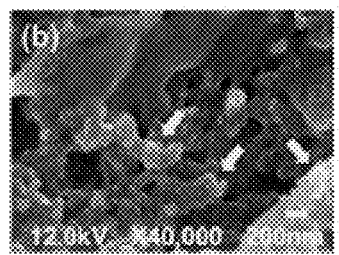

The nanostructured modified electrodes were studied using scanning electron microscopy. Imaging studies showed that the MWCNT were randomly distributed over the electrode forming a mesh like structure on the surface (FIG. 28a). Such a network of nanostructures can provide improved immobilization of the enzyme with reduced leaching. Deposition of Au nanoparticles on these nano-carbon functionalized electrode shows a more homogeneous conformation at 200 nm with the appearance of small globules (FIG. 28b), spreading across the electrode area. This comparatively uniform coating of Au on the working electrode will provide larger surface-volume ratio and enhance the conductivity of the biosensor with increased current signal.

Example 13—Bioelectrochemical Reaction of XO

XO, an oxidoreductase enzyme, with a flavin adenine dinucleotide (FAD) cofactor readily oxidases xanthine to UA. It has two molecules of FAD bridged by a pair of ferric mercaptide groups. Purine substrates bound by the isoalloxazine ring system of one FAD undergoes oxidation in the presence of $O_2$ and $H_2O$ (Eq. 10). This enzymatic oxidation of xanthine was quantified by measuring the formed $H_2O_2$. In this process, the $H_2O_2$ byproduct gets reduced (Eq. 11) on the MWCNT/Au matrix by exchanging electrons between the electrode and the reduction reaction, generating an electrical signal.

$$\text{Xanthine} + O_2 + H_2O \rightarrow \text{Uric acid} + H_2O_2 \quad (10)$$

$$H_2O_2 + 2H^+ + 2e^{-1} \rightarrow 2H_2O_2 \quad (11)$$

Figure 28C:
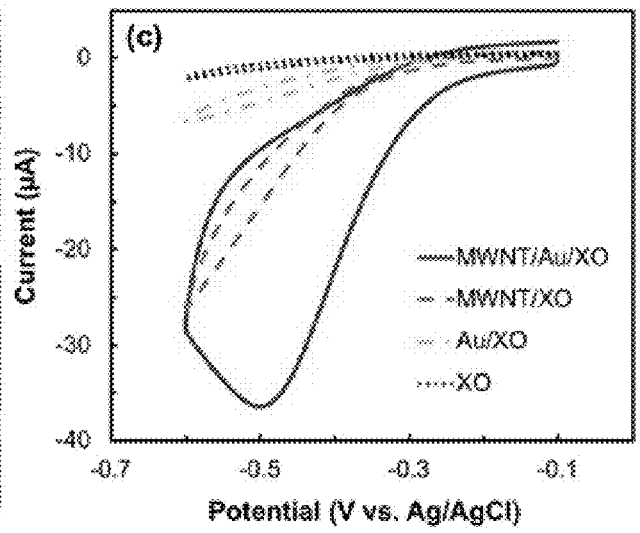
Figure 29:
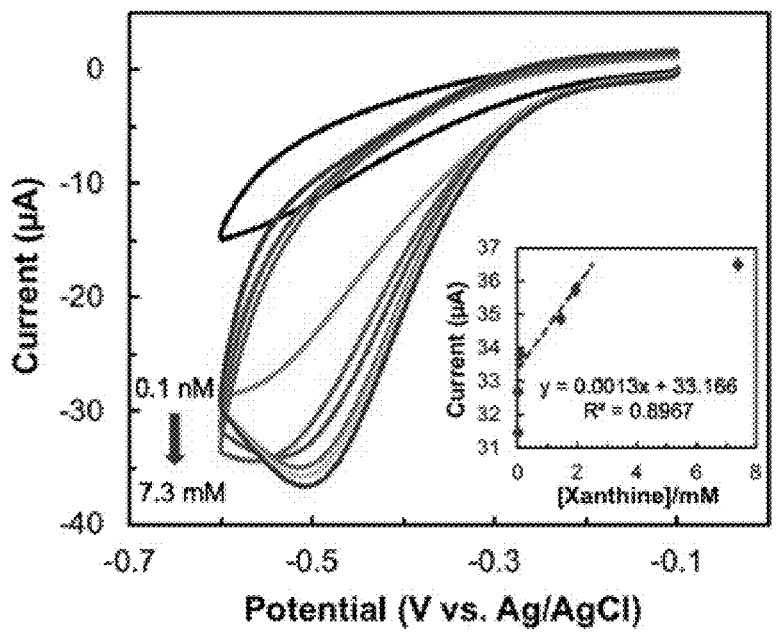
FIG. 29 shows CV signals of various xanthine concentrations from MWNT/Au/XO biosensor. Inset: Linear regression plot of the biosensor.

The xanthine reduction signal for MWNT/Au/XO nanocomposite sensor has the lower onset voltage (0.2 V) and with higher slope compared to XO on only MWNT, Au or bare electrodes (FIG. 28c) revealing the enhanced electrocatalytic properties. In the presence of xanthine, the nanocomposite has the peak at $Ep_c$ −0.5V, however no definite peak appeared for other three electrodes. It can be seen from the same figure that a MWNT/XO functionalized electrode provided higher signal for xanthine by 15 µA, owing to greater surface area as compared to Au/XO modified electrode. A combination of both MWCNT and Au nanoparticles however, was seen to provide significant response as compared to their use individually. At an $Ep_c$ −0.5 V, in the same concentration of xanthine, $Ip_c$ of 36.4 µA was observed from a MWCNT/Au/XO modified electrode (FIG. 29). This nanocomposite electrode offered a 36-fold increase in response as compared to other enzymatic electrodes.

The enzymatic response of such MWCNT/Au/XO modified electrodes was also studied with increasing concentrations of xanthine. Results showed that there was an increase in Ipc (at Epc −0.5 V) with respect to xanthine concentration, indicating that there was an electron transfer from $H_2O_2$ reduction to the electrode with respect to xanthine concentration. The concentrations tested were from 0.1 nM-7.3 mM. A linear increase in the Ipc with respect to xanthine is depicted in FIG. 29. Studies have shown the Ipc linearly increased from 11.2 µA to 36.5 µA as concentrations of xanthine increased. The nanocomposite modified XO electrode offered a sensitivity of 18.57 nA $µM^{-1}$ $cm^{-2}$ with enzyme activity retained through irreversible immobilization of the enzyme on its working area. The enzyme immobilization processes provided improved performance by 25 µA compared to other three electrodes with minimized leaching within its microenvironment, allowing diffusion of the analyte towards the working area of the transducer surface.

Example 14—Effect of pH on Enzyme Signal

Figure 30:
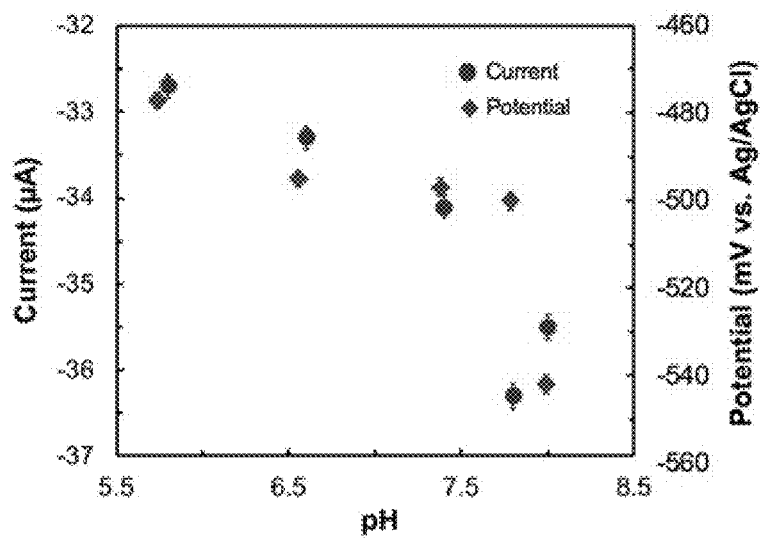
FIG. 30 shows the effect of pH on the current and potential of the biosensor.

It is known that enzymes are sensitive to pH and can denature over pH variations, providing higher activity and more stable performance at specific pH. XO is an enzyme, known to be active at alkaline pH. To understand the activity of XO and stability of performance, the electrochemical performance of the enzymatic biosensor was assessed over a broad pH range from 5.6 to 8.0 in the presence of 7.3 mM xanthine. Results have shown that stable performance was observed at higher pH as seen from FIG. 30, with increased current around pH 7.5. The peak potential was also seen to shift with respect to pH with higher electrochemical performance obtained between pH 7 and 8. This shows that this enzymatic biosensor can provide stable performance in this pH range, for greater shelf life. Wounds are also known to have a higher pH when severe and shift to the lower (pH 4) as they heal. The correlation of healing with pH can thus enable calibration of the enzymatic biosensor, as a potential surrogate towards wound monitoring.

Example 15—Miniaturized Electronics with Potentiostat

Figure 31:
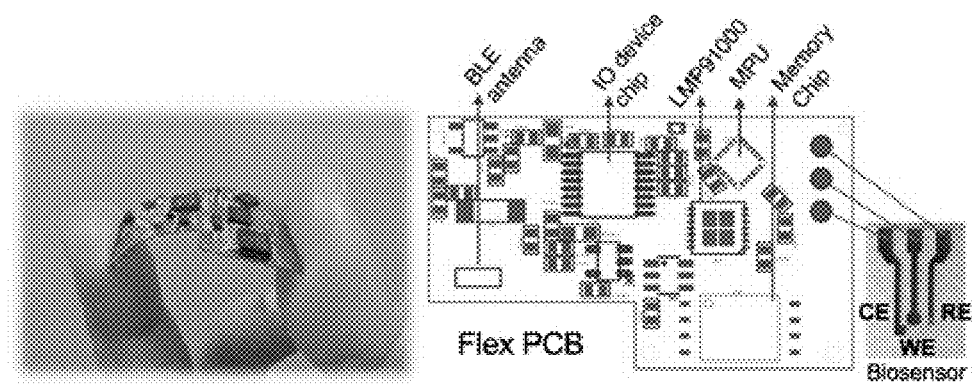
FIG. 31 shows electronics on flex (left). Schematic of circuit design and components on the PCB interfaced with the flexible sensor (right).

The XO enzymatic biosensor has been designed to be accommodated on a wearable platform. The platform composed of a miniaturized potentiostat (LMP91000) and a microcontroller (CC2650), integrated with a low power Bluetooth (BLE) for wireless data transmission. All electronic components with the analog front end (AFE), BLE antenna, and other associated circuitry has been interfaced with the sensor and mounted on a single top layer of the device as seen in FIG. 31. All three electrodes have been connected to corresponding pins of the AFE, linked to the microcontroller, CC2650. With a battery voltage regulated at 0.5 $V_{DC}$ from source to system, the current consumption of the system can be increased for optimum performance between 2 and 40 mA. Power consumption of the device shows, it depends not only on the amperometric operation of the potentiostat, but also on the BLE transmission and communication; along with the run time current drawn from the central processing unit (CPU). While the CPU runs for a shorter duration during BLE transmission conversion of the analog output from the potentiostat, the remaining time was used for other peripheral operations. It consumes an average power of ~56 µW over a 3.7 V and 350 mAh battery, providing a system operational lifetime of multiple days. These studies can thus pave a pathway for personalized wound diagnostics and continuous monitoring of healing, reducing surgeries and amputations Example 16—Assessing Wound Severity The biochemical pathways of purine metabolism in wounds can be used to assess and/or predict wound severity. Xanthine oxidase converts hypoxanthine to xanthine and subsequently leads to formation of uric acid. Xanthine oxidoreductase (XOR), is emerging as an important source stimulating production of reactive oxygen species (ROS) during healing, and xanthine oxidase (XO) is a complex oxidoreductase described as a key enzyme in purine catabolism, converting hypoxanthine to urate.

The correlation of purine precursors like hypoxanthine with wounds is well established. Reduced levels of xanthine have been observed in wounds from patients with severe wounds. Depletion in its levels has been revealed to promote dermal healing. Elevated levels of XO were detected in chronic venous leg ulcers, playing a crucial role in the healing process of wounds. Due to these recent observations, XO is considered as a potential biomarker for wound infection.

Through correlations with levels of hypoxanthine, this work discusses an enzymatic biosensor which has the potential to predict the severity of chronic wounds and track its pathway.

Figure 32:
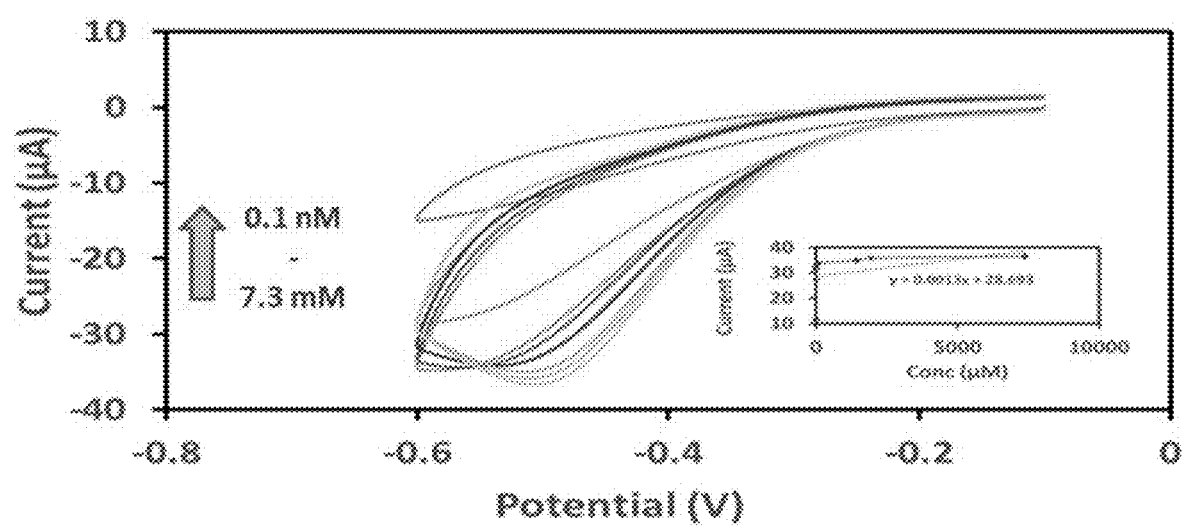
FIG. 32 shows a plot depicting the linear increase in response to increasing concentrations of Xanthine.

The enzymatic biosensor can entail use of metal nanomaterial (CNT/Au) to improve its sensing performance in detection of the analyte (FIG. 32). Linear change in response was observed with increasing concentrations of xanthine within the concerned physiological range (FIG. 32: inset). Results show its utility in not only monitoring the healing of wounds but also to track complications if any during recovery.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

We claim:

1. A flexible enzymatic electrochemical sensor comprising a working electrode, a reference electrode and a counter electrode, the working electrode being functionalized with an enzyme, the enzyme being selected from uricase (UOx), adenosine deaminase, arginase and xanthine oxidase (XO), the working electrode being further functionalized with a polymer and catalytic metal nano-structures selected from nano-flakes, nano-rods, and nano-wires.

2. The flexible enzymatic electrochemical sensor of claim 1, further comprising an electrode transfer mediator.

3. The flexible enzymatic electrochemical sensor of claim 2, the electrode transfer mediator being ferrocene carboxylic acid (FCA).

4. The flexible enzymatic electrochemical sensor of claim 1, the electrode being further deposited with a nano-structure.

5. The flexible enzymatic electrochemical sensor of claim 4, the nano-structure comprising multi-walled carbon nanotubes (MWCNTs).

6. The flexible enzymatic electrochemical sensor of claim 1, the polymer being Poly (vinyl alcohol) N-methyl-4(4'-formylstyryl)-pyridinium-metho-sulfate-acetal (PVA-SbQ).

7. The flexible enzymatic electrochemical sensor of claim 1, the enzyme being entrapped in the polymer with a polymer to enzyme ratio (v/v) of from 1:1 to 1:6.

8. The flexible enzymatic electrochemical sensor of claim 1, the working electrode being made of gold, silver, platinum or carbon.

9. The flexible enzymatic electrochemical sensor of claim 1, the working electrode being a carbon electrode functionalized with uricase (UOx), an ionic polymer and catalytic Ag nano-wires, UOx being entrapped in the ionic polymer, and the flexible enzymatic electrochemical sensor further comprising an electrode transfer mediator comprising FCA.

10. The flexible enzymatic electrochemical sensor of claim 1, the enzyme being adenosine deaminase.

11. The flexible enzymatic electrochemical sensor of claim 1, the enzyme being arginase.

12. The flexible enzymatic electrochemical sensor of claim 1, the working electrode being a carbon electrode functionalized with xanthine oxidase (XO), and MWCNTs on the surface.

13. A method for monitoring the healing of a wound comprising contacting a wound care substrate with a wound of a subject, the wound care substrate comprising a flexible enzymatic electrochemical sensor of claim 1; and measuring an electrical signal generated from a reaction between the flexible enzymatic electrochemical sensor and a biomarker in the wound, the biomarker being uric acid, adenosine, arginine and/or xanthine.

14. The method of claim 13, comprising applying the wound care substrate onto the wound, applying the wound care substrate in the vicinity of the wound, embedding the wound care substrate in the wound or a wound extract, contacting the wound care substrate with a biofluid of the wound, and/or embedding the wound care substrate in the biofluid of the wound.

15. The method of claim 14, the biofluid being sweat, plasma, blood, urine, tear, saliva, or serum.

16. A method for assessing wound severity comprising contacting a wound care substrate with a wound of a subject, the wound care substrate comprising a flexible enzymatic electrochemical sensor of claim 1; and measuring an electrical signal generated from a reaction between the flexible enzymatic electrochemical sensor and a biomarker in the wound, the biomarker being uric acid, adenosine, arginine and/or xanthine.

17. A flexible enzymatic electrochemical sensor, comprising a working electrode, a reference electrode and a counter electrode, the working electrode being a carbon electrode functionalized with uricase (UOx), PVA-SbQ, and catalytic nano-wires on the surface, UOx being entrapped in the matrix of PVA-SbQ, and the flexible enzymatic electrochemical sensor further comprising FCA.

* * * * *